United States Patent
Veige et al.

(10) Patent No.: US 8,889,879 B2
(45) Date of Patent: Nov. 18, 2014

(54) METHOD FOR LINKING TWO OR MORE METALS FOR PHOTO AND ELECTRONIC MATERIALS

(71) Applicant: University of Florida Research Foundation, Inc., Gainesville, FL (US)

(72) Inventors: Adam Steven Veige, Gainesville, FL (US); Trevor Del Castillo, Gainesville, FL (US); Leslie Justin Murray, Gainesville, FL (US); Xi Yang, Gainesville, FL (US); Andrew R. Powers, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 50 days.

(21) Appl. No.: 13/872,544

(22) Filed: Apr. 29, 2013

(65) Prior Publication Data

US 2013/0310568 A1 Nov. 21, 2013

Related U.S. Application Data

(63) Continuation of application No. PCT/US2011/057851, filed on Oct. 26, 2011.

(60) Provisional application No. 61/407,248, filed on Oct. 27, 2010.

(51) Int. Cl.
*C07F 1/12* (2006.01)
*C07F 9/50* (2006.01)

(52) U.S. Cl.
CPC ................. *C07F 1/12* (2013.01); *C07F 9/5045* (2013.01)
USPC ...................................................... 548/103

(58) Field of Classification Search
CPC .................................................... C07D 249/04
USPC ...................................................... 548/103
See application file for complete search history.

(56) References Cited

PUBLICATIONS

Chuang et al. "Solid state coordination chemistry of molybdenum oxides with 1,2,3-triazole (Htrz): The crystal structures of [Cu(I)Cu(II)2(trz)2Mo4O13(OH)], [MoO3(Htrz)0.5] and [Cu(I)trz]" Inorganica Chimica Acta (2008), 361(8), 2357-2364.*

Zhou et al. "Hydrothermal syntheses and structures of three novel coordination polymers assembled from 1,2,3-triazolate ligands" CrystEngComm (2009), 11(9), 1964-1970.*
Brady, S.E. et al., "Preparation of Polymers Containing Metal-Metal Bonds along the Backbone Using Click Chemistry," *J Inorg Organomet Polym*, 2010, pp. 511-518, vol. 20.
Chen, Z-F. et al., "Coordination polymers constructed by linking metal ions with azodibenzoate anions," *CrystEngComm*, 2008, pp. 217-231, vol. 10.
Eddaoudi, M. et al., "Systematic Design of Pore Size and Functionality in Isoreticular MOFs and Their Application in Methane Storage," *Science*, 2002, pp. 469-472, vol. 295.
Gadzikwa, T. et al., "Covalent surface modification of a metal-organic framework: selective surface engineering via Cu[1]-catalyzed Huisgen cycloaddition," *Chem. Comm.*, 2008, pp. 5493-5495.
Heinz, P. et al., "Clusters for alkyne-azide click reactions," *Dalton Transactions*, 2010, pp. 7640-7644, vol. 39.
Janczewski, D. et al., "Covalent assembly of functional inorganic nanoparticles by "click" chemistry in water," *Chem. Commun.*, 2010, pp. 3253-3255, vol. 46.
Partyka, D.V. et al., "Carbon-Gold Bond Formation through [3 + 2] Cycloaddition Reactions of Gold(I) Azides and Terminal Alkynes," *Organometallics*, 2007, pp. 183-186, vol. 26.
Del-Castillo, T.J. et al., "1,3-Dipolar cycloaddition between a metal-azide ($Ph_3PauN_3$) and a metal-acetylide ($Ph_3PAuC\equiv CPh$): an inorganic version of a click reaction," *Dalton Transactions*, 2011, pp. 8140-8144, vol. 40.
Fortman, G.C. et al., "A versatile gold synthon for acetylene C-H bone activation," *Dalton Transactions*, 2010, pp. 10382-10390, vol. 39.
Partyka, D.V. et al., "Copper-Catalyzed Huisgen [3 + 2] Cycloaddition of Gold(I) Alkynyls with Benzyl Azide. Synthesis, Structures, and Optical Properties," *Organometallics*, 2009, pp. 6171-6182, vol. 28.

* cited by examiner

*Primary Examiner* — Samantha Shterengarts
*Assistant Examiner* — Amanda L Aguirre
(74) *Attorney, Agent, or Firm* — Saliwanchik, Lloyd & Eisenschenk

(57) ABSTRACT

Embodiments of the invention are directed to bimetallic substituted triazole compounds and methods to prepare the compounds. The compounds include at least one 1,2,3-triazole that is substituted by two metal ions at the 1 and 4 or 5 positions of the triazole ring. An iClick reaction between a metal acetylide and a metal azide results in the bimetallic substituted triazole ring. Depending on the metal acetylide and the metal azide used, monomeric bimetallic substituted triazole compounds, oligomeric bimetallic triazole compounds, or polymeric bimetallic triazole compounds are formed. Polymeric bimetallic triazole compounds can be linear, branched, ladder, two-dimensional network, or three-dimensional networks.

18 Claims, 11 Drawing Sheets

METHOD FOR LINKING TWO OR MORE METALS FOR PHOTO AND ELECTRONIC MATERIALS

This application is a continuation-in-part of International Patent Application No. PCT/US2011/057851, filed Oct. 26, 2011, which claims the benefit of U.S. Provisional Patent Application Ser. No. 61/407,248, filed Oct. 27, 2010, the disclosures of which are hereby incorporated by reference in their entirety.

BACKGROUND OF INVENTION

A Click reaction is one that yields a product quantitatively or nearly so while being tolerant to a wide range of solvents, including water, and pH conditions and having a strong thermodynamic driving force. These characteristics are attractive when designing new approaches to building small molecules and materials. Reactions that have the characteristics of a Click reaction were originally pursued in the field of drug discovery, and the approach has led to an immense number of potential drug targets in a manner that is easier and less expensive than earlier synthetic approaches used for drug discovery.

Of the reactions that are classified as Click reactions, the most recognized and prolifically applied is the copper catalyzed azide-alkyne cycloaddition (CuAAC) to yield 1,4-disubstituted 1,2,3-triazoles, as shown in Scheme 1, below. This reaction is particularly accessible due to: the ease of synthesis of the alkyne and azide functional reactants in nearly quantitative yields; the tolerance of the reaction to a wide variety of solvents, including water; the regioselectivity of the reaction toward synthesis of 1,4-disubstituted triazoles; and the high tolerance of alkyne and azide functional groups to most other functional groups. CuAAC represents the qualities of a Click reaction so well that it is often referred to simply as "the click reaction".

Scheme 1

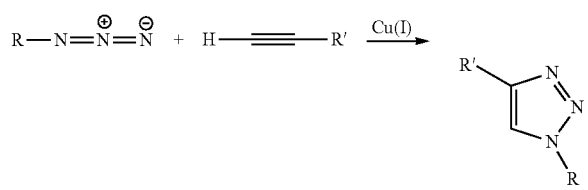

Despite the great activity of Click Chemistry and, particularly, CuAAC, there are few applications of these reactions in inorganic or organometallic chemistry. CuAAC has been applied to the functionalization metal clusters with organic moieties and to the synthesis of organic ligands to be employed with metal ions. Neither the CuAAC nor any Huisgen 1,3-dipolar cycloaddition reaction has not been explored to directly link two or more metal ions. Organobimetallic and multimetallic compounds employing the cycloaddition of metal-azides and metal-acetylides should be useful as bimetallic catalysts, polymers, and 2- or 3-dimensional covalent metal organic networks, including those where a plurality of identical or different metals are isolated and at least two metals are separated by a 1,2,3-triazole ring.

BRIEF SUMMARY

Embodiments of the invention are directed to bimetallic substituted triazole compounds comprising one or more 1,2,3-triazole units where at least one of the triazole units is substituted by two metal ions in the 1 and 4 or 5 positions. The triazole units can be further substituted with an organic substituent in the 4 or the 5 position that is not substituted by the metal ion. The metal ions can be Au, Ni, Pd, Pt, Ru, Fe, Mn, Rh, Ir, Cr, Cu,W or any other group 3-16 metal. The compound can include at least one ligand attached to at least one metal ion, where the ligand can be, for example, a phosphorous based ligand, nitrogen based ligand, cyclopentadienyl derivative, carbon monoxide, nitrosyl, alkyl, aryl, or pincer-type ligand that can be neutral or charged and monodentate, bidentate, polydentate and bridging or chelating. In some embodiments of the invention, a plurality of triazole units is present with at least one metal attached to two triazole units. In other embodiments of the invention a multiplicity of triazole units are connected by a multiplicity of metal ions as a linear polymeric chain or a polymeric network. According to an embodiment of the invention, metal-clusters with one or more azide and/or one or more acetylide groups can be used. The use of metal comprising compounds in cycloaddition reactions, incorporates an inorganic component to the process and products. Hence, the reaction is an "inorganic click" or "iClick" reaction. According to embodiments of the invention, the iClick reaction can proceed uncatalyzed, as in Huisgen 1,3-dipolar cycloadditions, or can proceed in the presence pf a copper(I) catalyt.

Other embodiments of the invention are directed to a method for the preparation of the bimetallic substituted triazole compounds where at least one metal acetylide and at least one metal azide are combined and undergo cycloaddition to form a triazole ring. The metal azide can be a metal with 1 to 6 azide groups and the metal acetylide can be a metal with 1 to 6 acetylide groups, which can be unsubstituted or substituted with an organic group.

DETAILED DISCLOSURE

Figure 1:
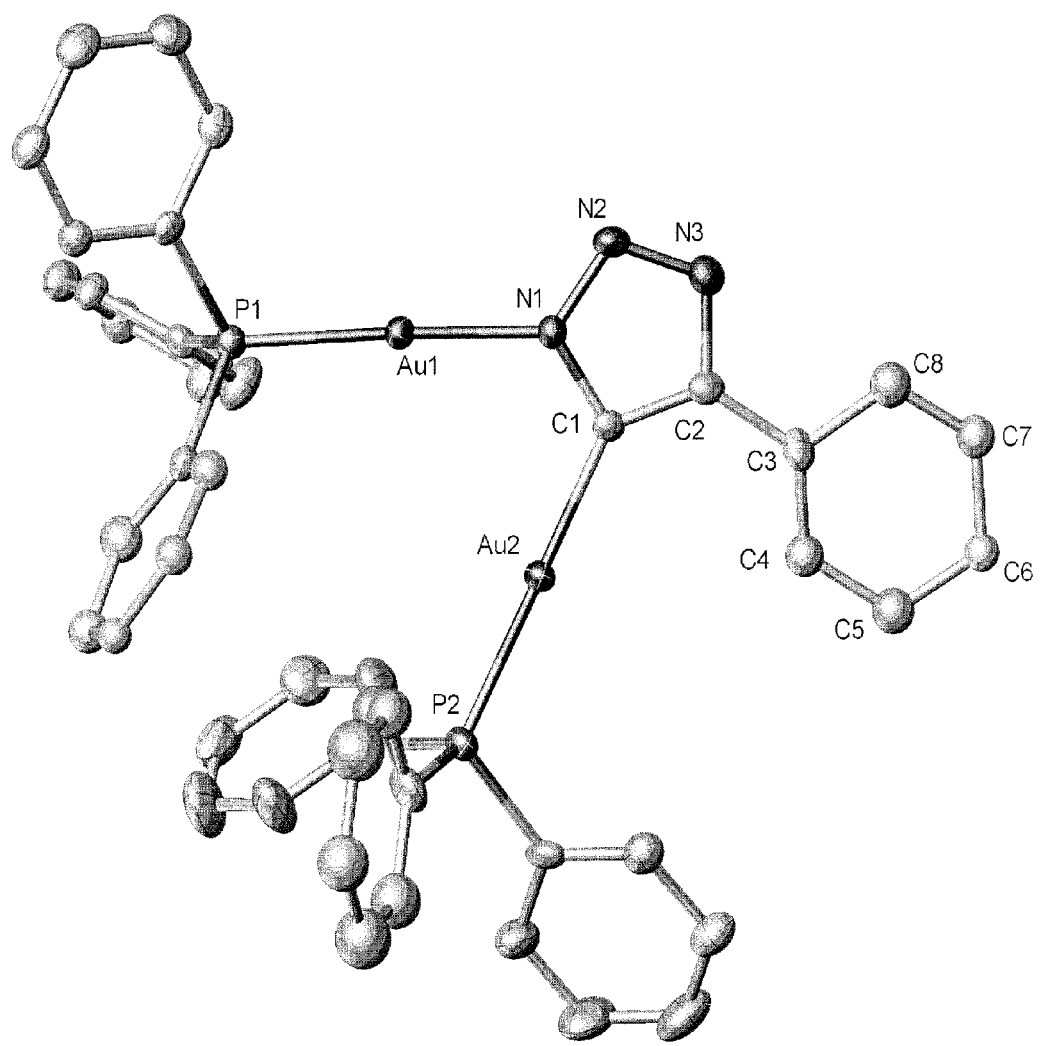
FIG. 1 shows the molecular structure of homobimetallic triazole complex $3_{1,5}$, according to an embodiment of the invention, as determined by single crystal X-ray diffraction experiments.

Embodiments of the invention are directed to a method, an iClick reaction, where 1,3-dipolar cycloaddition is employed to link two or more metal ions upon combining a metal-coordinated azide complex and a metal-coordinated alkyne complex with the formation of a 1,4-bimetallic substituted 1,2,3-triazole, as shown in Scheme 2, below, for reaction between a metallic monoacetylide and a metallic monoazide where M and M' represent metal centers that can be the same metal or different metals, L is independently any ligand, and R is hydrogen or any organic substituent. In other embodiments of the invention, the cycloaddition can result in a 1,5-bimetallic substituted triazole, as shown in Scheme 3, or a combination of 1,4- and 1,5-bimetallic substituted triazole. The selectivity towards 1,4- or 1,5-addition depends upon the metal ion or ions and other substituents on the acetylide and whether the reaction employs copper(I) as a catalyst. In embodiments of the invention, one or both of M and M', the metal centers, are not a single metal ion, rather, M and/or M' is a cluster complex where a plurality of one metal ion or a plurality of two or more metal ions reside as a cluster. In these embodiments of the invention, one or more metal ions of the cluster are bonded to at least one azide or to at least one acetylide. Although other ligands need not be present, the cluster can have one or more ligands, such as, but not limited to, carbon monoxide, halides, isocyanides, alkenes, or hydrides, included to stabilize the cluster complex.

Embodiments of the invention are directed to bimetallic complexes, trimetallic complexes, one-dimensional metallopolymers and metallooligomers, two-dimensional metal-organic networks, and three-dimensional metallo-networks formed from azide and acetylide reagents. Each of these products, according to embodiments of the invention, can vary by the number and identity of the combined metal ions, ligands, regioselectivity of the addition product, coordination geometries, oxidation states, and redox combinations that permit these organometallic species to be used in a variety of applications. Currently, methods for linking two metal ions are limited, and linking two or more metal ions in a controllable fashion is difficult. The iClick reaction has a strong thermodynamic driving force that effectively couples nearly any metal azide and any metal acetylide rapidly and displays a quantitative or nearly quantitative efficiency. The iClick reaction can be catalyzed. For example, a catalytic amount of copper (I) salt can be added to the reaction mixture, or formed in the reaction mixture by the addition of a copper (II) salt and copper metal or other reducing agent.

Scheme 2

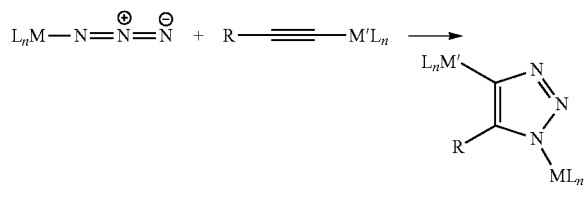

Scheme 3

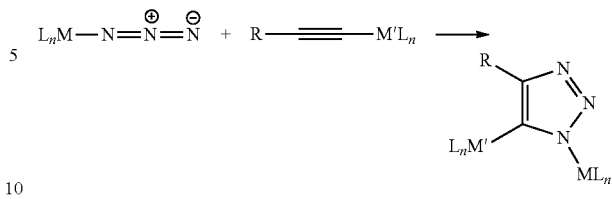

For bimetallic triazoles, as illustrated in Schemes 2 and 3, the metal ions, M and M' are independently a metal from groups 3-12 or a main group metal from groups 13-16. For example, the metal ions can be Au, Ni, Pd, Pt, Ru, Fe, Mn, Rh, Ir, Cr, Cu, and/or W ions. Ligands can be neutral or charged and can be monodentate, bidentate or polydentate and chelating a single metal or bridging a plurality of metals. Common ligands include but are not limited to: phosphorous based ligands; nitrogen based ligands, including pyridine, bipyridine, and terpyridine; cyclopentadienyl derivatives; carbon monoxide; nitrosyl; alkyl; aryl; and pincer-type ligands. In some embodiments of the invention, the ligand can include functional groups to permit their association or bonding to a surface, incorporation into a resin, or polymerization to materials with fixed bimetallic triazole units for use as heterogeneous catalysts.

In these bimetallic triazoles, the R group can be H, $C_1$-$C_{30}$ alkyl, $C_6$-$C_{22}$ aryl, $C_7$-$C_{30}$ alkylaryl, $C_7$-$C_{30}$ arylalkyl, $C_2$-$C_{29}$ heteroaryl, $C_3$-$C_{30}$ alkylheteroaryl, $C_3$-$C_{30}$ heteroarylalkyl, $C_2$-$C_{30}$ alkenyl, $C_8$-$C_{30}$ alkenylaryl, $C_8$-$C_{30}$ arylalkenyl, $C_4$-$C_{30}$ alkenyiheteroaryl, or $C_4$-$C_{30}$ heteroarylalkenyl and can be attached at any possible carbon of the R group to the triple bond of the reagent acetylide and the C—C double bond of the product triazole. Alkyl groups can be linear, branched, multiply branched, cyclic, polycyclic, or any combination thereof. Aryl groups can be phenyl, fused ring, for example, a naphthyl group, or multi-ring, for example, biphenyl groups, with any geometry or substitution pattern. Alkylaryl groups are those connected to the triple bond of the reagent acetylide at any carbon of an aryl ring, which is substituted with one or more alkyl groups, where an alkyl portion can be an alkylene chain disposed between two aryl portions. Arylalkyl groups are those connected to the triple bond of the reagent at any carbon of the alkyl portion and have one or more aryl groups attached at any carbon of the alkyl portion or inserted within the alkyl portion of the group. Heteroaryl groups contain one or more five-membered or larger aromatic heterocyclic rings where one or more heteroatoms, for example, O, N, or S, are included in the aromatic ring and can be a single ring, fused rings, or multi-ring, where one or more ring of the fused or multi-ring group has one or more heteroatoms. Alkenyl groups can have one or more double bonds situated anywhere in the group where multiple double bonds can be isolated, conjugated, or a mixture of isolated and conjugated double bonds and where the alkenyl group can be a vinyl group or an internal double bond with any E or Z in geometry or any combination of vinyl with E or Z geometry for multiple double bonds. Any R groups can be substituted at any position with, for example, nitro, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $CO_2H$, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $NH_2$, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl)amino, $C_8$-$C_{30}$ (arylalkynyl)amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl)amino, $C_7$-$C_{30}$ di(arylalkyl)amino, $C_8$-$C_{30}$ alkyl(arylalkyl)amino, $C_{15}$-$C_{30}$ aryl(arylalkyl)amino, $C_8$-$C_{30}$ alkenyl(aryl)amino, $C_8$-$C_{30}$ alkynyl(aryl)amino $C(O)NH_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, $C_1$-$C_{30}$ hydroxyalkyl, $C_6$-$C_{14}$ hydroxyaryl, $C_7$-$C_{30}$ hydroxyarylalkyl, $C_3$-$C_{30}$ hydroxyalkenyl, $C_3$-$C_{30}$ hydroxyalkynyl, $C_8$-$C_{30}$ hydroxyarylalkenyl, $C_8$-$C_{30}$ hydroxyarylalkynyl, $C_3$-$C_{30}$ polyether, $C_3$-$C_{30}$ polyetherester, $C_3$-$C_{30}$ polyester $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester $C_3$-$C_{30}$alkylsulfonic acid, $C_3$-$C_{30}$alkylsulfonate salt, $C_1$-$C_{30}$ carboxylate salt, thiocarboxylate salt, dithiocarboxylate salt or $C_3$-$C_{30}$alkyl$C_1$-$C_4$ trialkyammonium salt. Asymmetric functional groups, such as ester and amido, can have either orientation with respect to their orientation relative to the triazole ring. Heteroatoms in substituents can be at any position of those substituents, for example, oxygen of an ether or ester or nitrogen of an amine or amide can be in the alpha, beta, gamma or any other position relative to the point of attachment to the base portion of the R group. Heteroatom containing substituents can have a plurality of heteroatoms; for example, ether can be a monoether, a diether or a polyether, amine can be a monoamine, a diamine or a polyamine, ester can be a monoester, a diester, or a polyester, and amide can be a monoamide, a diamide or a polyamide. Ethers and esters groups can be thioethers, thioesters and hydroxy groups can be thiol (mercapto) groups, where sulfur is substituted for oxygen. Salts can be those of alkali or alkali earth metals, ammonium salts, or phosphonium salts.

In an embodiment of the invention, linear metallopolymers can be formed by the addition of trans-diazide octahedral complexes with trans-diacetylide octahedral complexes, as shown below in Scheme 4. Inclusion or substitution of other geometries, for example, cis-diazide and cis-diacetylide octahedral complexes, or disubstituted tetrahedral complexes, allows for the preparation of cyclic or macrocyclic metallopolymers. These metallopolymers can display extended electron delocalization through multiple metal centers linked by triazole rings. Such conjugated polymers can be used in applications that exploit their non-linear optical properties, such as optical signal processing, switching, and frequency generation in optical data storage, optical communication, and optical image generation devices. Variation in the triazole structure allows control of the effective π conjugation length in these polymers, which determines the polymer's optical gap. The structure of R is as for the bimetallic triazoles described above. As a plurality of metallic diacetylide and metallic diazide can be used, a plurality of different Ms and/or M's can be included in a single polymer. The metals can be any selected from group 3-12 metals and main group metals from groups 13-16. For example, the metals can be Au, Ni, Pd, Pt, Ru, Fe, Mn, Rh, Ir, Cr, Cu, and/or W. A plurality of different R groups can be used, where a single metallic diacetylide has two different R groups, an asymmetric metallic diacetylide, or when two or more different metallic diacetylides are used where the diacetylides are symmetric, asymmetric, or any combination thereof. Polymers with different degrees of polymerization can be formed by varying the ratio of the metallic diacetalide and metallic diazide reagents, for example, a ratio of n/n+1 or n+1/n to yield azide end-groups or acetalide end-groups, respectively. The linear metallopolymer, which can be considered a linear metallooligomer, is formed when n/n+1 is relatively small, for example, when n/n+1 is about 9/9+1 or less. The metallooligomers can be cyclic oligomers or a mixture of linear and cyclic metallooligomers.

Scheme 4

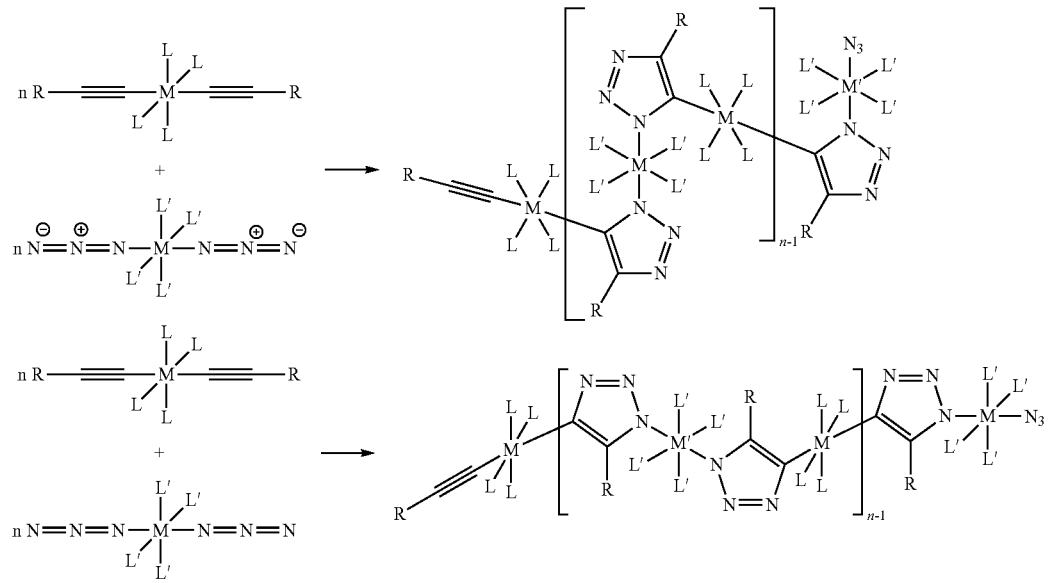

In another embodiment of the invention, one or more metallic monoacetylides and/or metallic monoazides are included with the metallic diacetylides and metallic diazides to control the degree of polymerization of the metallopolymers. In one embodiment of the invention, when one or more metallic monoacetylides are employed, a portion of the R groups can have functionality appropriate for use of the metallopolymers or metallooligomers as macromers for a second polymerization. The functional R groups can be only on metallic monoacetylides or they can be included in a portion of the metallic diacetylides. For example, a vinyl group, such as an acrylate, methacrylate, or styrene group can be included of a two-dimensional network using reaction between square planar metal centers where ligands are omitted for clarity in the illustrated product. The 1,4-substituted trizole linkages occurs in the presence of a copper(I) catalyst.

Scheme 5

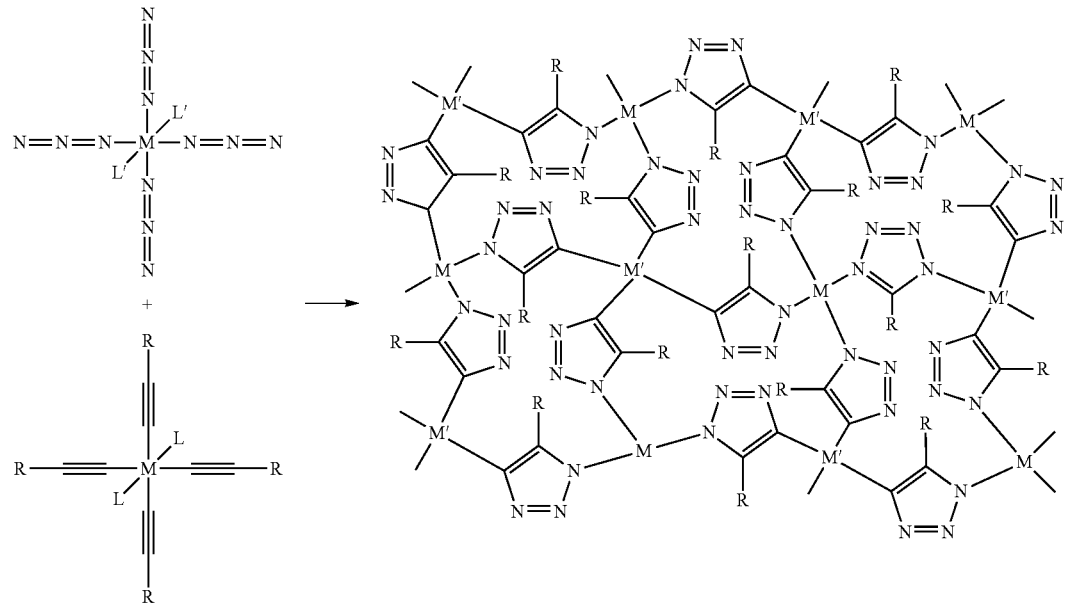

in the metallic monoacetylides, or a cyclic ether, for example, an epoxide, can be included for an addition chain growth polymerization of the macromer, or its copolymerization with a second monomer with like or copolymerizable group for crosslinking the metallopolymer or inclusion of the metallopolymer, into a resin at a small quantity. In another embodiment of the invention, the R groups of a portion of the metallic monoacetylides can include functionality that allows the linear metallopolymers or linear metallooligomers to be used as a macromer by a condensation or addition step growth polymerization with a complementary monomer. Alternatively an organic diacetylide and/or an organic diazide can be included into the iClick reaction mixture with the metallic diacetylides and metallic diazides to decouple the effective π conjugation length from the degree of polymerization of the polymer, where the proportion of metallic diacetylides and metallic diazides to all diacetylides and diazides defines the conjugation length while the proportions of all diazides to all diacetylides define the molecular weight of the linear polymer. By inclusion of metallic or organic tri-, tetra-, penta-, or hexaacetylides and/or metallic or organic tri-, tetra-, penta-, or hexatriazides into the mixture of diazides and diacetylides, networks can be formed.

In another embodiment of the invention the iClick reaction between: metal tetraazides and metal tetraacetylides; metal tetraazides and metal diacetylides; metal diazides and metal tetraacetylides; metal triazides and metal triacetylides; metal triazides and metal diacetylides; or metal diazides and metal triacetylides results in the formation of a two-dimensional network when the R groups are small; for example, hydrogen or methyl as the acetylide and azides are coplanar with the metal ions. Ladder polymer can result in some embodiments of the invention where metal triacetylides and/or metal triazides are included. Scheme 5, below, illustrates the formation In some embodiments of the invention, 2-dimensional networks can be synthesized by reaction of mixtures of metal complexes that include cis-, trans-, and/or mer-acetylide or azido complexes, with or without included square planar metal complexes, where the 2-dimensional networks are of finite proportions and are effectively nanoparticle sized sheets or flakes rather than the extended sheets that can be considered larger "bulk" materials. Such nanoparticulate two-dimensional networks can be employed as heterogeneous catalysts, as-synthesized compound or after post-synthesis modification, such as after metal ion doping or controlled oxidation, or as photo-induced catalysts where the network is generated with hetero-metal centers with photochemistry tuned by the ligands, for example, bipyridines or terpyridines, on the metal center. Use of trans-diacetylides or azides employed with square planar tetraacetylides or tetraazides in a complementary manner can result in "bulk" two-dimensional networks. These "bulk" two-dimensional networks share some features with metal organic frameworks (MOFs), such that they can be used as heterogeneous catalysts or as surfaces for gas storage. Thin films of the two-dimensional polymers can be grown or spin-coated after synthesis onto electrode surfaces for use as electrocatalysts for redox reactions due to simultaneous conductivity and catalytic activity. The two-dimensional iClick formed materials are advantageous over MOFs due to: the presence of strong covalent metal-carbon and metal-nitrogen bonds rather than the dative interactions of MOFs; surfaces where different metal ions residing in specific coordination environments rather than MOFs which inherently lack site specificity; mononuclear metal nodes having strict geometric constraints due to the geometry imposed by the reactant acetylide and azide complexes; and the order imposed by a 2-dimensional network from iClick reactions that occur at ambient temperatures rather than those for MOFs where synthesis is typically carried out under hydrothermal conditions at elevated temperatures.

In another embodiment of the invention, three-dimensional networks are formed via copper(I) catalysis, where either homoleptic azides or acetylides, in octahedral or tetrahedral geometries, are paired with their complementary trans-di-acetylide or diazide, as shown in Schemes 6 and 7, below. Scheme 6 illustrates a network from a hexaacetylide and a diazide, where ligands are not shown in the network for easier view, that has a cubic cell. Scheme 7 shows only the reagent mixture, but does not show the diamond-like cell of the resulting network imposed by the tetrahedral geometry of one of the reagents. These materials have some similar properties as those for zeolitic imidazolate frameworks (ZIFs), which include high porosity and stability. Three-dimensional networks from iClick reactions are readily directed toward a specific utility through the choice of substituent on the acetylide ligand(s) and by modification of the two N-donor coordination sites that are available in the three-dimensional network. The three-dimensional networks can be constructed for use as gas storage/separation network, size-selective heterogeneous catalysts, or lithium ion battery separators.

Scheme 6

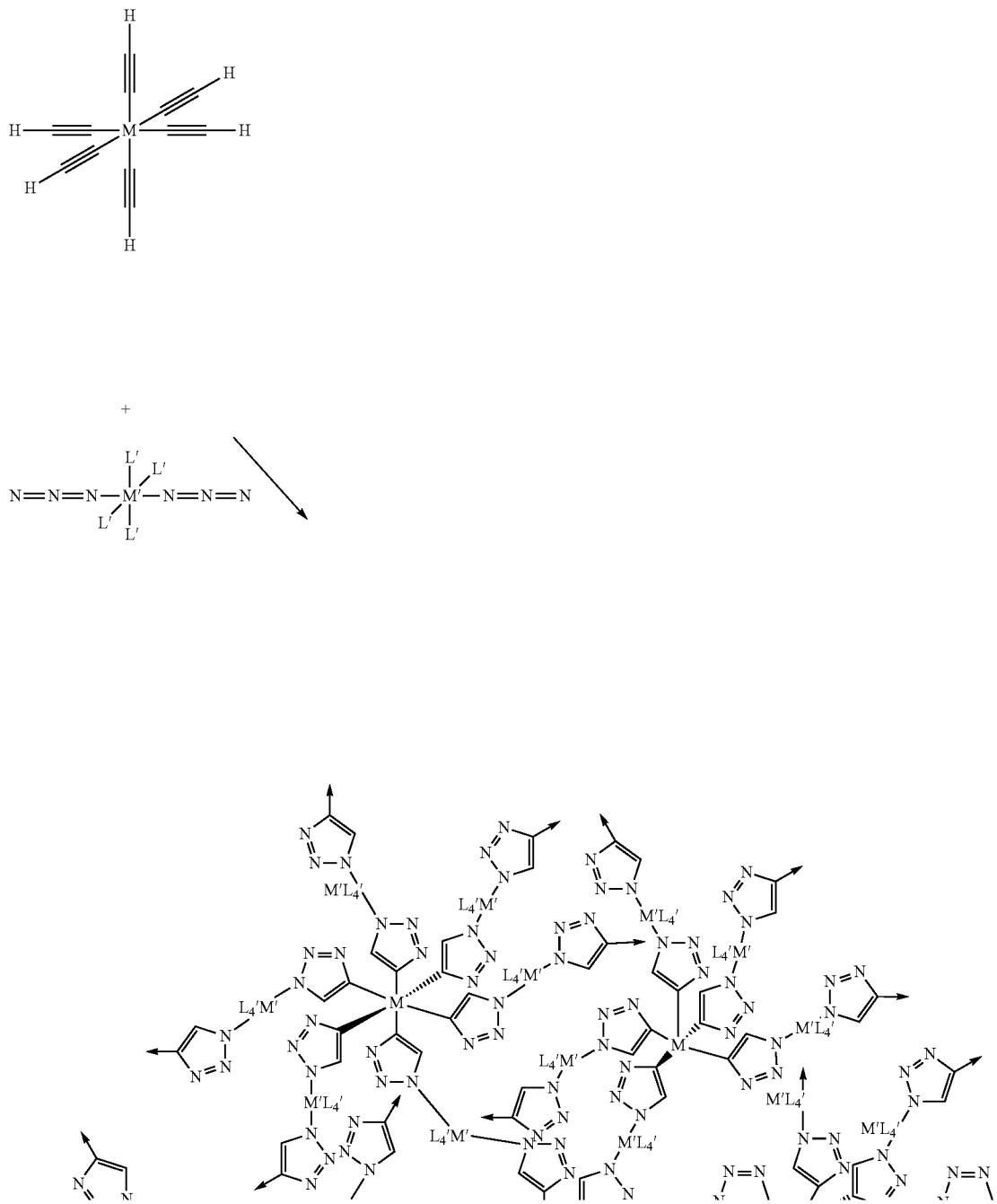

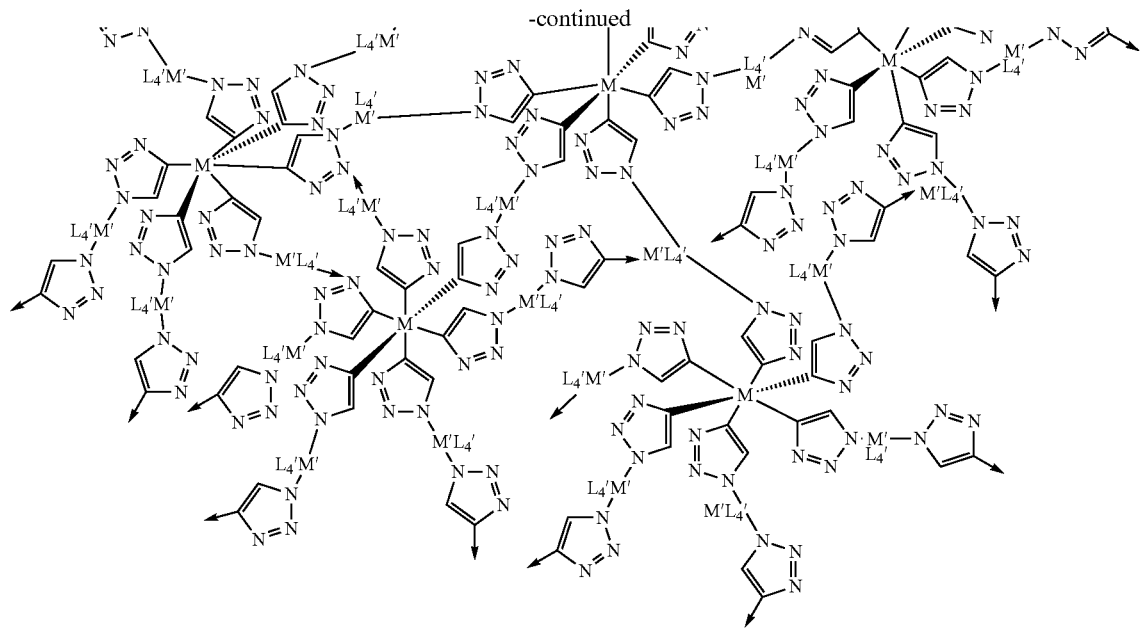

-continued

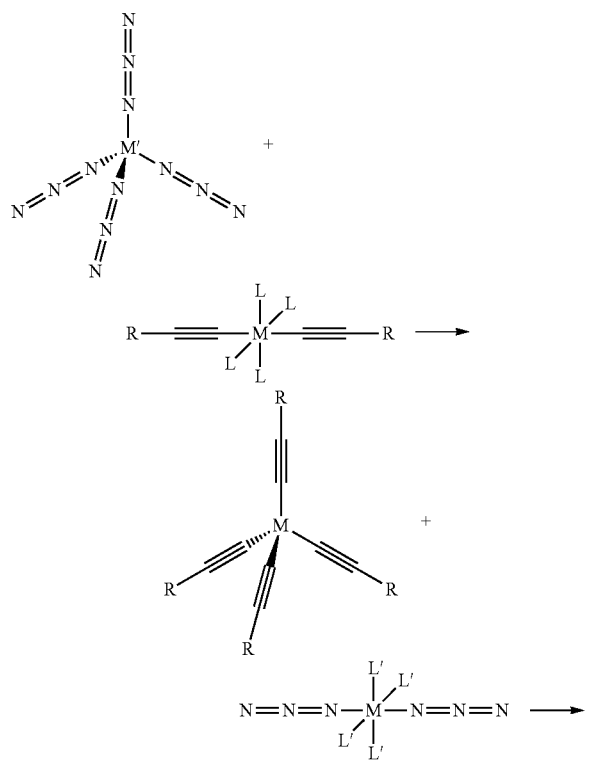

Scheme 7

Methods and Materials

General Methods

Glassware was oven dried before use. Unless otherwise specified, all manipulations were performed under an inert atmosphere using standard Schlenk or glove-box techniques. Pentane, toluene, methylene chloride, and diethyl ether ($Et_2O$) were degassed by sparging with high purity argon and dried using a Glass Contours drying column. Methanol was dried over anhydrous copper(II)sulfate, distilled and stored over 4 Å molecular sieves. Benzene-$d_6$ and chloroform-$d_1$ (Cambridge Isotopes) were dried over sodium-benzophenone ketyl and distilled or vacuum transferred and stored over 4 Å molecular sieves. Commercially available $PPh_3AuCl$ and $TMSN_3$ were used without further purification. Commercially available phenylacetylene was distilled before use. The following materials were purchased and used as received: chloro(dimethylsulfide)gold(I) (Sigma-Aldrich); chloro(triethylphosphine)gold(I) (Sigma-Aldrich); triphenylphosphine (Acros); cis-dichlorobis(triethylphosphine)platinum (II) (Sigma-Aldrich); potassium tetrachloroplatinate(II) (Aldrich), 1-ethynyl-4-nitrobenzene (Sigma-Aldrich); 1,1-bis(diphenylphosphino)methane (dppm) (Sigma-Aldrich); sodium azide (Acros). $Ph_3PAuCCPh$, $Ph_3PAuN_3$, $PPh_3Au$—$C\equiv CPh$, cis-$(PPh_3)_2PtCl_2$, cis-$(PPh_3)_2Pt(N_3)_2$ (4-Ph), $PPh_3Au$—Cl, $PPh_3Au^IC\equiv CC_6H_4NO_2$ (5-Ph), cis-$(PEt_3)_2Pt(N_3)_2$ (4-Et), and $PEt_3Au^IN_3$ (9), $[Au(\mu$-dppm$)Cl]_2$ were prepared according to literature procedures. NMR spectra were obtained on Varian Mercury Broad Band 300 MHz, Varian Mercury 300 MHz, or on Varian Inova 500 MHz spectrometers. Chemical shifts are reported in δ (ppm). For $^1H$ and $^{13}C\{^1H\}$ NMR spectra, the solvent resonance was referenced as an internal reference, and for $^{31}P\{^1H\}$ NMR spectrum, the 85% $H_3PO_4$ resonance was referenced as an external standard. Elemental analyses were performed at Complete Analysis Laboratory Inc., Parsippany, N.J. FT-IR spectra were recorded on a Thermo scientific instrument.

Synthesis of a Homo-bimetallic Complex

Figure 2:
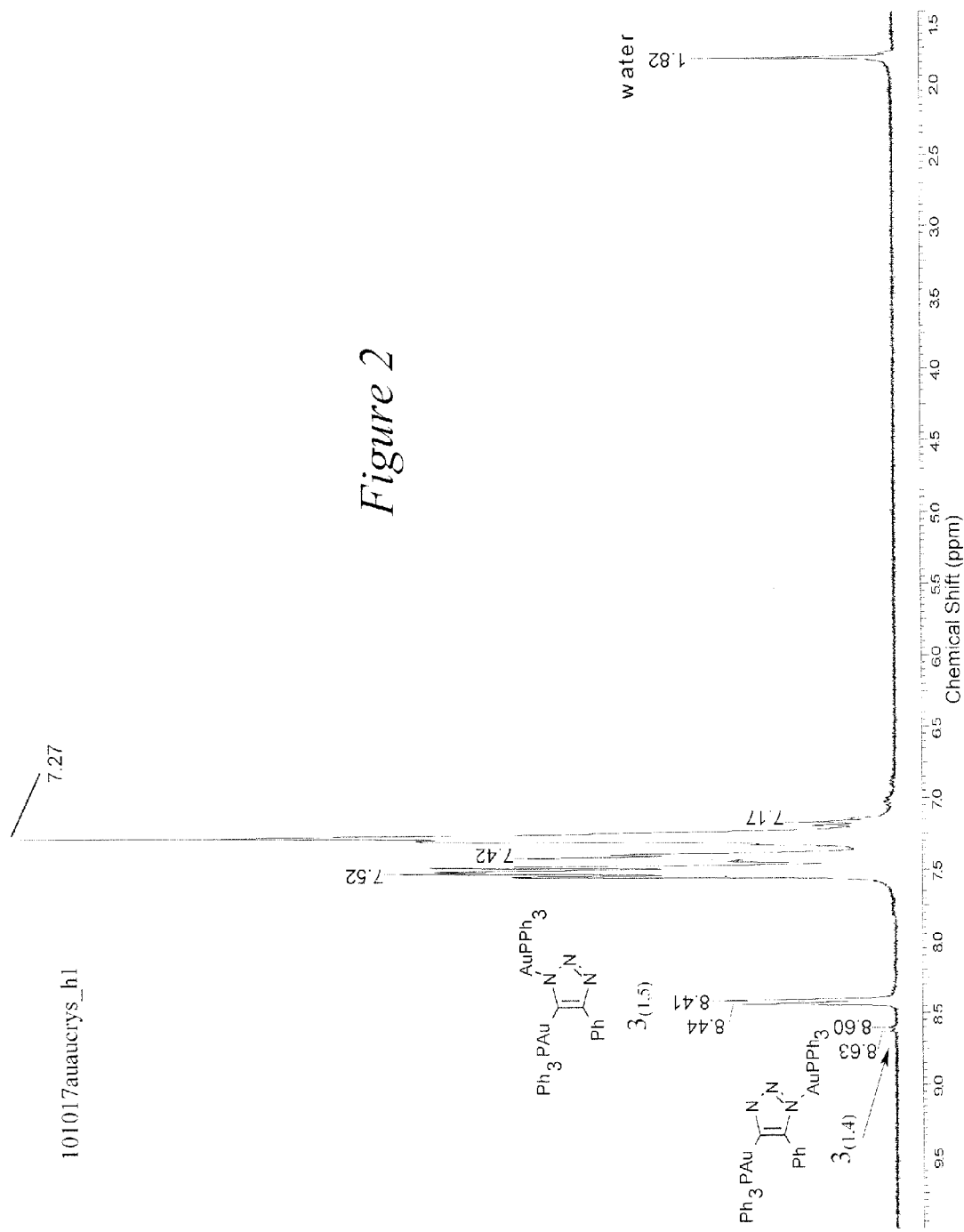
FIG. 2 shows a $^1$H NMR spectrum of a mixture of $3_{1,5}$ and $3_{1,4}$ according to an embodiment of the invention in CDCl$_3$.
Figure 3:
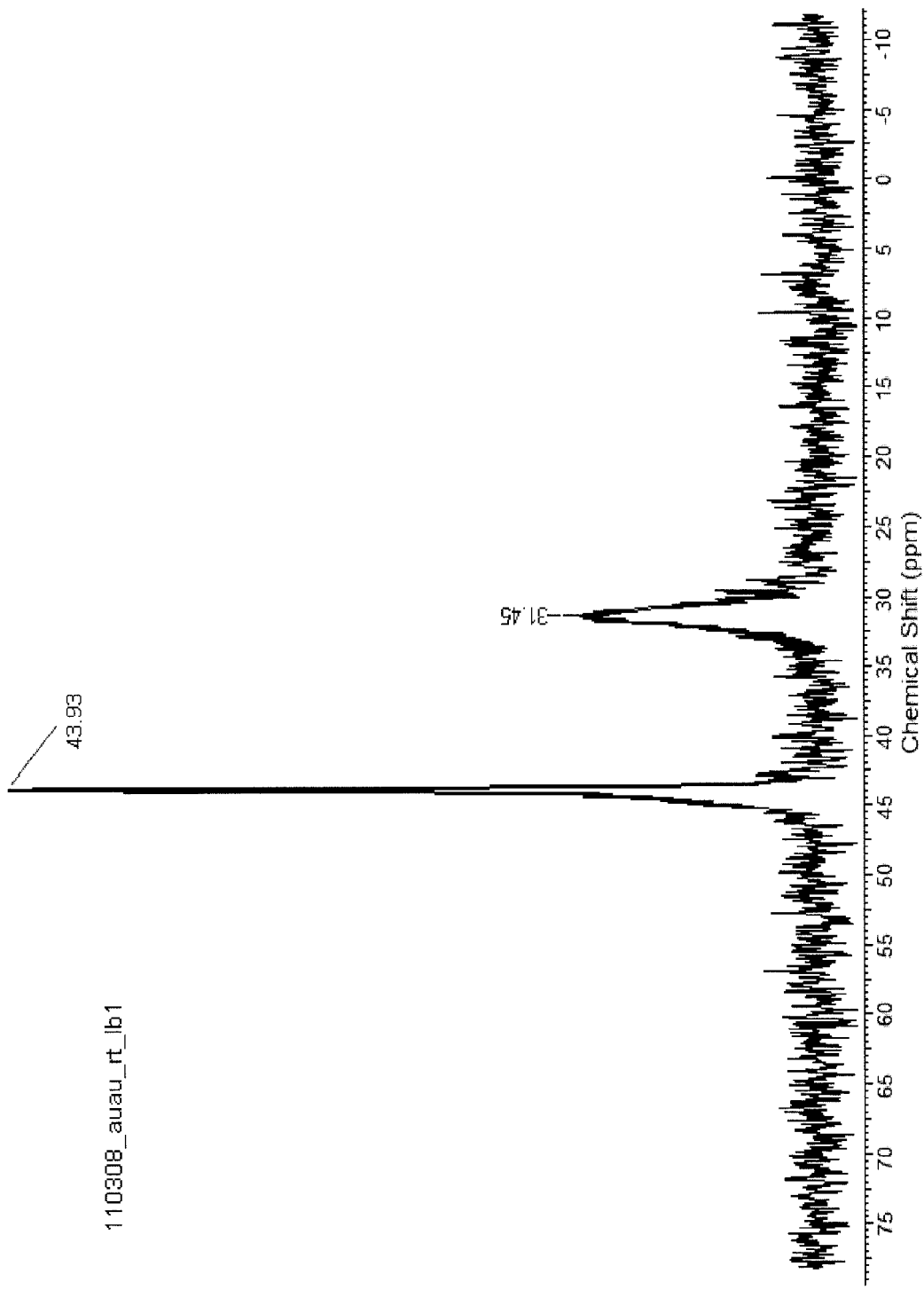
FIG. 3 shows a $^{31}$P{$^1$H} NMR spectrum of a mixture of $3_{1,5}$ and $3_{1,4}$, according to an embodiment of the invention referenced to PPh$_3$ as an external standard.
Figure 4:
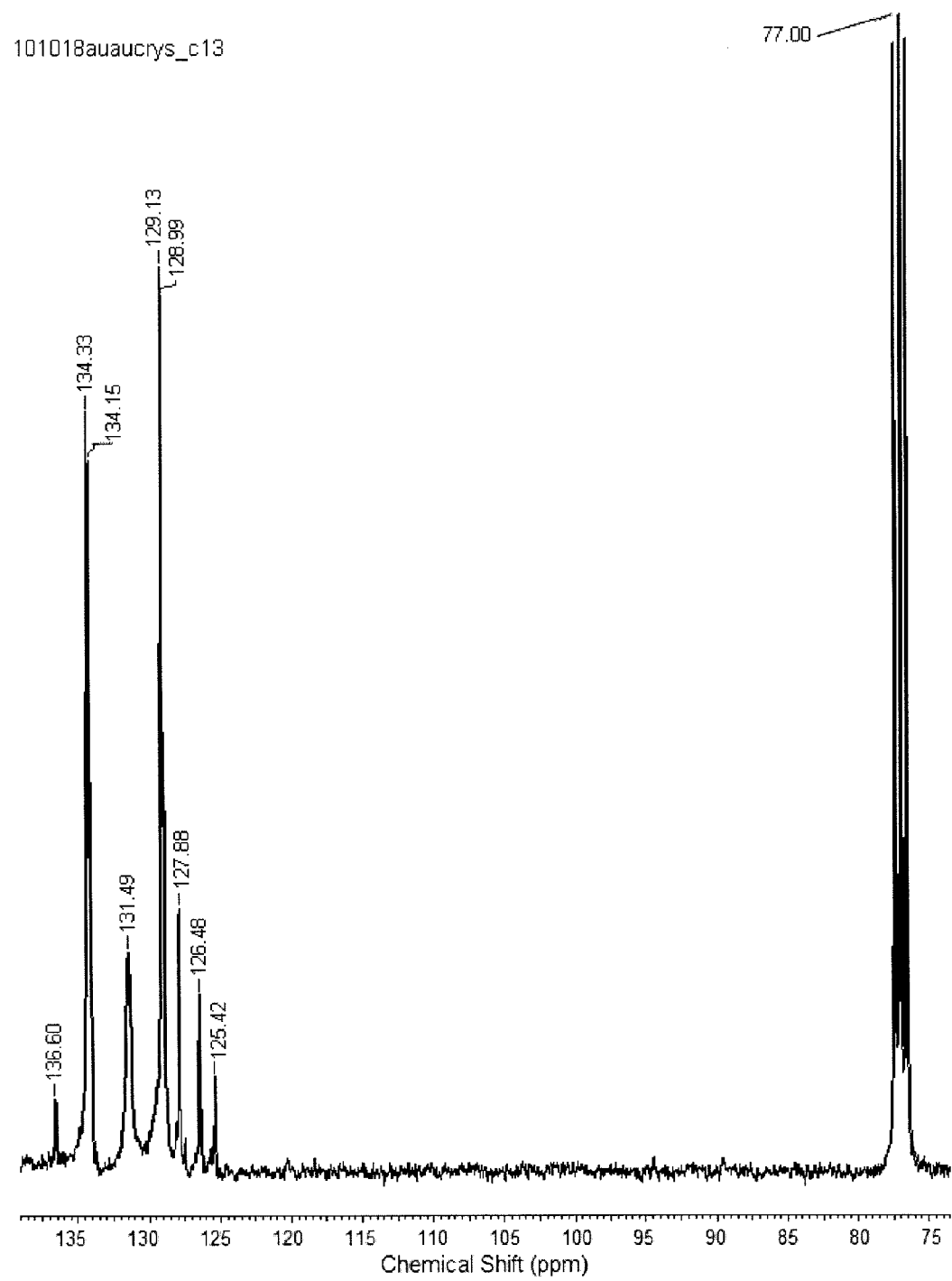
FIG. 4 shows a $^{13}$C{$^1$H} NMR spectrum of a mixture of $3_{1,5}$ and $3_{1,4}$ according to an embodiment of the invention.
Figure 5:
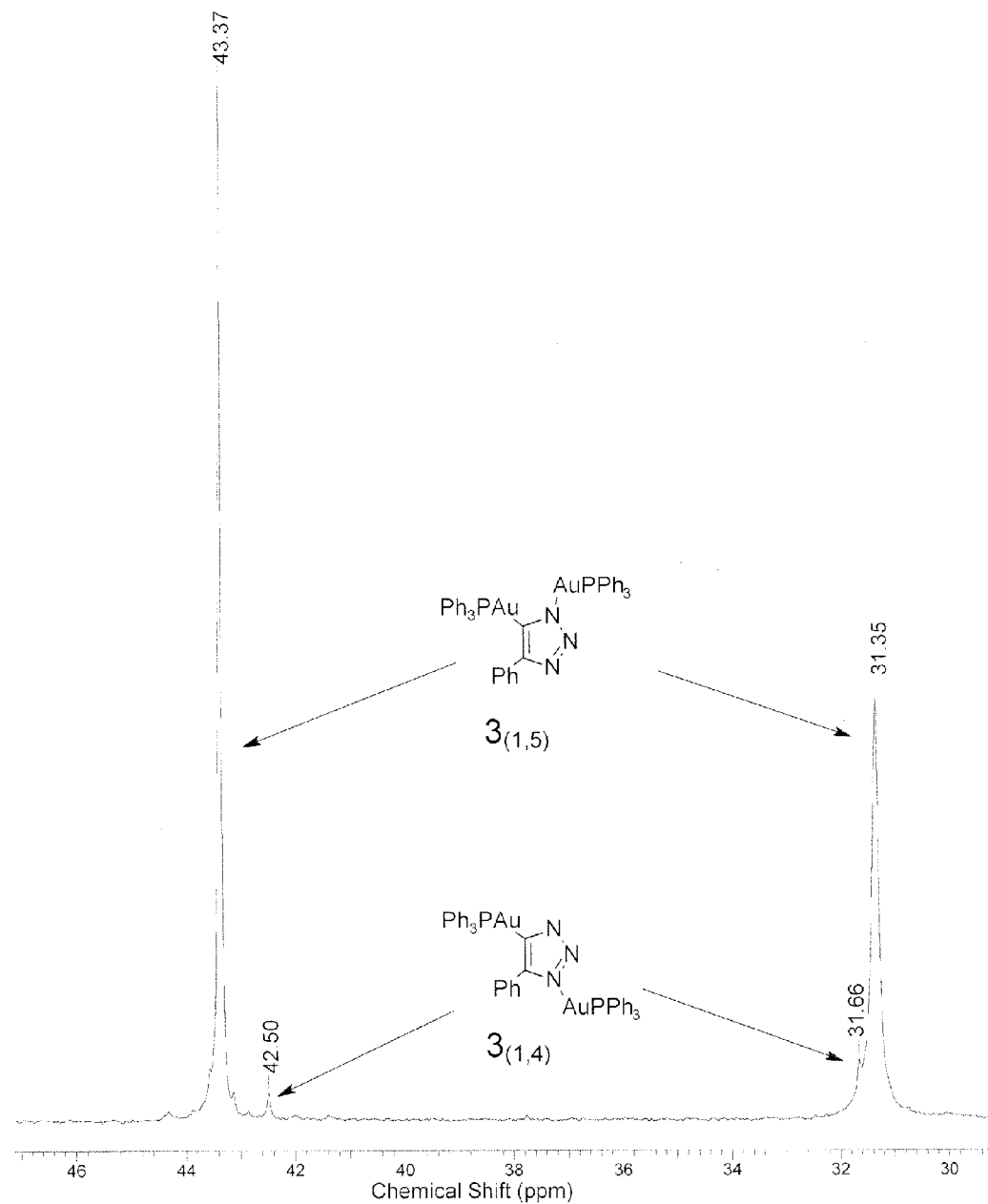
FIG. 5 shows a $^{31}$P{$^1$H} NMR spectrum of a mixture of $3_{1,5}$ and $3_{1,4}$ at −40° C. according to an embodiment of the invention.
Figure 6:
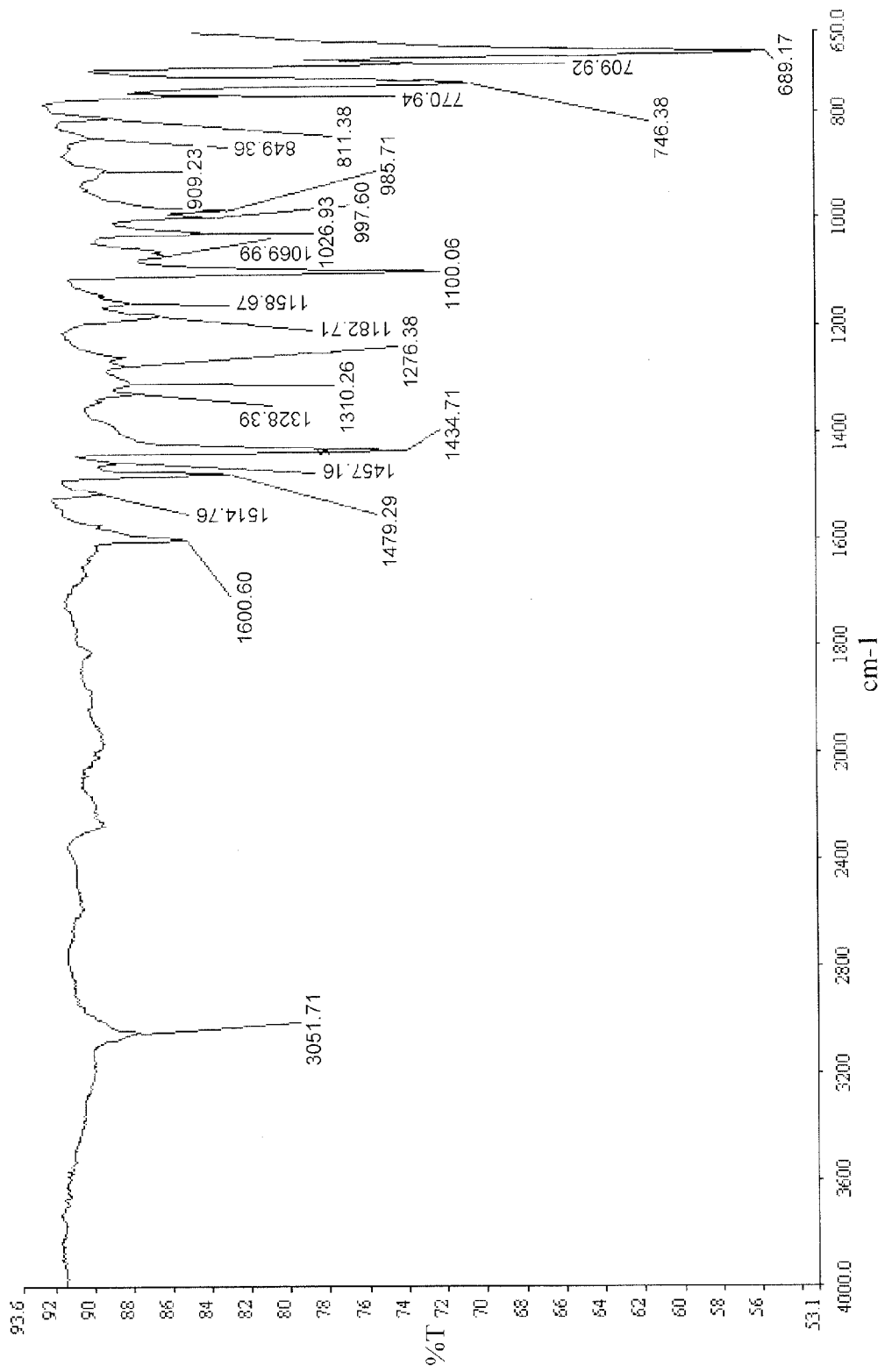
FIG. 6 shows a FT-IR spectrum of a mixture of $3_{1,5}$ and $3_{1,4}$, according to an embodiment of the invention.

As shown in Scheme 8, below, a sealable NMR tube was charged with 2 (10 mg, 0.018 mmol), 1 (9 mg, 0.018 mmol), and benzene-$d_6$ (0.6 mL). After 24 hours clear colorless crystals deposit. Crystals were collected and washed with pentane to give the major product $3_{1,5}$ and <3% minor product $3_{1,4}$ (17 mg, 89% yield). $3_{(1,5)}$: FIG. 1 shows the molecular structure of $3_{1,5}$ from single crystal X-ray diffraction. Tables 1 through 4, below, give crystal structure data for $3_{1,5}$ and Tables 5 and 6, below, give computationally determined geometries for $3_{1,5}$ and $3_{1,4}$. Additional support for the identification of complex $3_{1,5}$ comes from NMR spectroscopy. FIG. 2 is a $^1$H NMR spectrum of $3_{1,5}$ and $3_{1,4}$ in CDCl$_3$, FIG. 3 is a $^{31}$P{$^1$H} NMR spectrum of $3_{1,5}$ and $3_{1,4}$, and FIG. 4 is a $^{13}$C{$^1$H} NMR spectrum of $3_{1,5}$ and $3_{1,4}$. Two resonances appear in the $^{31}$P NMR spectrum at 43.93 and 31.45 ppm for the two distinct phosphorous nuclei on complex $3_{1,5}$. Cooling the solution to −40° C. reveals two addition P resonances attributable to $3_{1,4}$ (FIG. 5). FIG. 6 is an IR spectrum of $3_{1,5}$ and $3_{1,4}$ mixture. $^1$H NMR (300 MHz, CDCl$_3$), δ (ppm): 8.43 (d, J=9 Hz), 7.1-7.6 (m, aromatic). $^{31}$P{$^1$H} NMR (121.16 MHz, CDCl$_3$, 25° C.), δ (ppm): 43.93 (bs, PAuC), 31.45 (bs, PAuN). $^{13}$C{$^1$H} NMR (75 MHz, CDCl$_3$), δ (ppm): 136.6 (s, C$_{aromatic}$, triazolate), 134.2 (d, J$_{PC}$=14 Hz, o-C, overlapping, C—Au—P(C$_6$H$_5$)$_3$ and N—Au—P(C$_6$H$_5$)$_3$, 131.5 (bs, i-C, overlapping, C—Au—P(C$_6$H$_5$)$_3$ and N—Au—P(C$_6$H$_5$)$_3$, 129.1 (d, J$_{PC}$=11 Hz, m-C and p-C, overlapping, C—Au—P(C$_6$H$_5$)$_3$ and N—Au—P(C$_6$H$_5$)$_3$, 127.9 (s, C$_{aromatic}$, triazolate), 126.4 (s, C$_{aromatic}$, triazolate), 125.4 (s, C$_{aromatic}$, triazolate). $3_{(1,4)}$: $^1$H NMR (300 MHz, CDCl$_3$), δ (ppm): 8.6 (d, J=9 Hz), aromatic resoances overlapping with $3_{(1,5)}$ between 7.1-7.6. $^{31}$P{$^1$H} NMR (121.16 MHz, CDCl$_3$, −40° C.), δ (ppm): 43.93 (s, PAuC), 31.45 (s, PAuN). Anal. Calcd. for C$_{44}$H$_{35}$N$_3$P$_2$Au$_2$: C, 49.78; H, 3.32; N, 3.96. Found: C, 49.86; H, 3.41; N, 3.88.

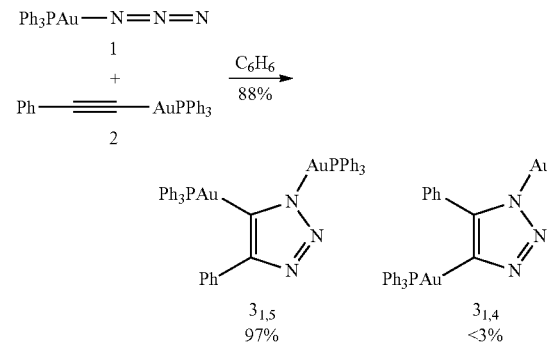

Scheme 8

TABLE 1

Atomic coordinates (× 10$^4$) and equivalent isotropic displacement parameters (Å$^2$ × 10$^3$) for $3_{1,5}$. U(eq) is defined as one third of the trace of the orthogonalized Uij tensor.

| Atom | x | y | z | U(eq) |
|---|---|---|---|---|
| Au1 | 8914(1) | 5890(1) | 3253(1) | 19(1) |
| Au2 | 8468(1) | 5595(1) | 4198(1) | 21(1) |
| P1 | 8059(1) | 6682(1) | 2920(1) | 19(1) |
| P2 | 7329(1) | 6217(1) | 4476(1) | 27(1) |
| N1 | 9633(2) | 5158(2) | 3574(1) | 20(1) |
| N2 | 10267(2) | 4683(2) | 3452(1) | 28(1) |
| N3 | 10514(2) | 4236(2) | 3737(1) | 28(1) |
| C1 | 9453(3) | 5018(2) | 3941(1) | 18(1) |
| C2 | 10022(3) | 4430(3) | 4039(1) | 21(1) |
| C3 | 10111(3) | 4014(3) | 4390(1) | 25(1) |
| C4 | 9562(7) | 4050(8) | 4675(3) | 29(3) |
| C5 | 9657(7) | 3636(8) | 5001(3) | 34(3) |
| C6 | 10293(7) | 3069(8) | 5028(4) | 25(3) |
| C7 | 10815(9) | 2945(7) | 4711(4) | 30(4) |
| C8 | 10753(10) | 3388(7) | 4404(4) | 33(4) |
| C4' | 9782(6) | 4390(7) | 4735(3) | 25(3) |
| C5' | 9847(6) | 4009(8) | 5075(3) | 32(3) |
| C6' | 10228(7) | 3316(8) | 5104(4) | 30(3) |
| C7' | 10589(9) | 2975(7) | 4803(4) | 31(3) |

TABLE 1-continued

Atomic coordinates (× 10$^4$) and equivalent isotropic displacement parameters (Å$^2$ × 10$^3$) for $3_{1,5}$. U(eq) is defined as one third of the trace of the orthogonalized Uij tensor.

| Atom | x | y | z | U(eq) |
|---|---|---|---|---|
| C8' | 10536(9) | 3355(8) | 4438(4) | 29(4) |
| C9 | 7056(3) | 5810(3) | 4930(1) | 27(1) |
| C10 | 6202(3) | 5729(3) | 5055(2) | 44(2) |
| C11 | 6043(4) | 5396(4) | 5400(2) | 55(2) |
| C12 | 6722(4) | 5145(4) | 5621(2) | 51(2) |
| C13 | 7564(3) | 5234(3) | 5505(2) | 38(1) |
| C14 | 7729(3) | 5565(3) | 5157(1) | 31(1) |
| C15 | 7538(3) | 7231(2) | 4558(1) | 38(1) |
| C16 | 7101(8) | 7607(3) | 4845(2) | 49(3) |
| C17 | 7308(12) | 8371(3) | 4935(2) | 61(4) |
| C18 | 7952(10) | 8760(3) | 4738(2) | 51(4) |
| C19 | 8388(6) | 8385(4) | 4451(4) | 62(5) |
| C20 | 8181(5) | 7620(4) | 4361(3) | 41(5) |
| C16' | 7358(18) | 7658(9) | 4912(6) | 49(6) |
| C17' | 7669(19) | 8424(9) | 4966(4) | 46(6) |
| C18' | 8250(20) | 8724(10) | 4711(5) | 60(6) |
| C19' | 8434(12) | 8337(10) | 4380(6) | 51(8) |
| C20' | 8057(16) | 7605(9) | 4319(5) | 42(8) |
| C21 | 6341(3) | 6148(3) | 4206(2) | 34(1) |
| C22 | 5706(4) | 6716(4) | 4190(2) | 61(2) |
| C23 | 4951(4) | 6592(5) | 3991(2) | 75(2) |
| C24 | 4816(3) | 5920(4) | 3801(2) | 57(2) |
| C25 | 5428(3) | 5343(4) | 3812(2) | 48(2) |
| C26 | 6184(3) | 5459(3) | 4014(2) | 42(1) |
| C27 | 7690(3) | 7506(3) | 3190(1) | 21(1) |
| C28 | 6876(7) | 7739(8) | 3238(4) | 35(3) |
| C29 | 6655(7) | 8402(8) | 3454(4) | 31(3) |
| C30 | 7316(8) | 8862(7) | 3584(3) | 21(3) |
| C31 | 8153(9) | 8664(7) | 3518(3) | 27(3) |
| C32 | 8363(8) | 8009(7) | 3328(4) | 26(3) |
| C28' | 6852(6) | 7477(8) | 3359(4) | 23(3) |
| C29' | 6579(8) | 8106(9) | 3569(4) | 34(4) |
| C30' | 7072(10) | 8729(9) | 3619(4) | 37(4) |
| C31' | 7899(12) | 8748(10) | 3464(5) | 46(5) |
| C32' | 8195(10) | 8115(9) | 3251(5) | 36(4) |
| C33 | 8582(3) | 7108(3) | 2517(1) | 19(1) |
| C34 | 8365(3) | 7843(3) | 2378(1) | 24(1) |
| C35 | 8780(3) | 8130(3) | 2065(1) | 29(1) |
| C36 | 9408(3) | 7694(3) | 1890(1) | 33(1) |
| C37 | 9624(3) | 6971(3) | 2023(1) | 31(1) |
| C38 | 9219(3) | 6676(3) | 2338(1) | 25(1) |
| C39 | 7120(3) | 6174(3) | 2733(1) | 20(1) |
| C40 | 6770(3) | 6362(3) | 2393(1) | 23(1) |
| C41 | 6122(3) | 5905(3) | 2238(1) | 30(1) |
| C42 | 5813(3) | 5265(3) | 2423(1) | 29(1) |
| C43 | 6139(3) | 5086(3) | 2771(2) | 38(1) |
| C44 | 6798(3) | 5532(3) | 2924(2) | 36(1) |
| C45 | 4057(4) | 3795(4) | 2519(2) | 57(2) |
| C46 | 3524(4) | 4396(4) | 2590(2) | 58(2) |
| C47 | 3201(4) | 4522(3) | 2931(2) | 59(2) |
| C48 | 3421(4) | 4032(4) | 3221(2) | 66(2) |
| C49 | 3987(4) | 3406(4) | 3150(2) | 58(2) |
| C50 | 4295(3) | 3310(4) | 2801(2) | 52(2) |
| C51 | 7654(5) | 7447(4) | 1222(5) | 44(4) |
| C52 | 7543(5) | 6747(5) | 1410(2) | 36(3) |
| C53 | 6862(7) | 6255(4) | 1315(2) | 42(3) |
| C54 | 6291(6) | 6464(5) | 1032(2) | 40(4) |
| C55 | 6402(5) | 7165(6) | 844(2) | 45(3) |
| C56 | 7083(5) | 7656(5) | 939(3) | 37(5) |
| C51' | 7545(5) | 7313(6) | 1200(3) | 51(5) |
| C52' | 7268(6) | 6586(6) | 1321(3) | 57(4) |
| C53' | 6457(7) | 6308(4) | 1217(3) | 40(3) |
| C54' | 5924(6) | 6758(5) | 991(2) | 34(3) |
| C55' | 6201(5) | 7485(5) | 869(2) | 40(3) |
| C56' | 7012(6) | 7762(4) | 974(3) | 64(7) |

TABLE 2

Bond lengths (in Å) for $3_{1.5}$.

| Bond | Length | Bond | Length | Bond | Length |
|---|---|---|---|---|---|
| Au1-N1 | 2.032(3) | C39-C44 | 1.392(6) | C51'-C52' | 1.39(1) |
| Au1-P1 | 2.2416(12) | C40-C41 | 1.385(6) | C51'-C56' | 1.39(1) |
| Au2-C1 | 2.035(4) | C41-C42 | 1.370(6) | C52'-C53' | 1.39(1) |
| Au2-P2 | 2.2846(12) | C7'-C8' | 1.465(19) | C53'-C54' | 1.39(1) |
| P1-C27 | 1.807(5) | C9-C14 | 1.386(7) | C54'-C55' | 1.39(1) |
| P1-C33 | 1.808(4) | C9-C10 | 1.399(7) | C55'-C56' | 1.39(1) |
| P1-C39 | 1.819(4) | C10-C11 | 1.384(8) | | |
| P2-C15 | 1.796(4) | C11-C12 | 1.381(8) | | |
| P2-C21 | 1.810(5) | C12-C13 | 1.373(7) | | |
| P2-C9 | 1.820(5) | C13-C14 | 1.394(7) | | |
| N3-N2 | 1.332(5) | C15-C20' | 1.337(18) | | |
| N3-C2 | 1.365(5) | C15-C16 | 1.39(1) | | |
| N1-N2 | 1.346(5) | C15-C20 | 1.39(1) | | |
| N1-C1 | 1.368(5) | C15-C16' | 1.49(2) | | |
| C1-C2 | 1.383(6) | C16-C17 | 1.39(1) | | |
| C2-C3 | 1.457(6) | C17-C18 | 1.39(1) | | |
| C3-C8' | 1.319(14) | C18-C19 | 1.39(1) | | |
| C3-C4 | 1.327(11) | C19-C20 | 1.39(1) | | |
| C3-C8 | 1.463(16) | C16'-C17' | 1.415(14) | | |
| C3-C4' | 1.486(11) | C17'-C18' | 1.376(14) | | |
| C4-C5 | 1.377(14) | C18'-C19' | 1.393(15) | | |
| C5-C6 | 1.385(16) | C19'-C20' | 1.402(14) | | |
| C6-C7 | 1.410(17) | C21-C22 | 1.384(6) | | |
| C7-C8 | 1.34(2) | C21-C26 | 1.390(7) | | |
| C4'-C5' | 1.387(13) | C22-C23 | 1.382(7) | | |
| C5'-C6' | 1.330(15) | C23-C24 | 1.357(8) | | |
| C6'-C7' | 1.349(17) | C24-C25 | 1.370(7) | | |
| C27-C28 | 1.429(12) | C25-C26 | 1.387(7) | | |
| C27-C32 | 1.439(13) | C27-C32' | 1.323(15) | | |
| C28-C29 | 1.419(14) | C27-C28 | 1.329(11) | | |
| C29-C30 | 1.372(16) | C42-C43 | 1.381(7) | | |
| C30-C31 | 1.356(17) | C43-C44 | 1.386(6) | | |
| C31-C32 | 1.354(16) | C45-C46 | 1.345(8) | | |
| C28'-C29' | 1.385(15) | C45-C50 | 1.362(9) | | |
| C29'-C30' | 1.324(18) | C46-C47 | 1.339(9) | | |
| C30'-C31' | 1.39(2) | C47-C48 | 1.380(9) | | |
| C31'-C32' | 1.41(2) | C48-C49 | 1.409(9) | | |
| C33-C38 | 1.388(6) | C49-C50 | 1.350(8) | | |
| C33-C34 | 1.400(6) | C51-C52 | 1.39(1) | | |
| C34-C35 | 1.383(6) | C51-C56 | 1.39(1) | | |
| C35-C36 | 1.375(7) | C52-C53 | 1.39(1) | | |
| C36-C37 | 1.373(7) | C53-C54 | 1.39(1) | | |
| C37-C38 | 1.387(6) | C54-C55 | 1.39(1) | | |
| C39-C40 | 1.373(6) | C55-C56 | 1.39(1) | | |

TABLE 3

Bond angles (°) for $3_{1.5}$.

| Bond | Angle | Bond | Angle | Bond | Angle |
|---|---|---|---|---|---|
| N1-Au1-P1 | 176.9(1) | C4-C3-C2 | 125.6(6) | C22-C21-C26 | 117.3(5) |
| C1-Au2-P2 | 177.99(12) | C8'-C3-C8 | 13.7(9) | C22-C21-P2 | 124.8(5) |
| C27-P1-C33 | 104.6(2) | C4-C3-C8 | 116.1(9) | C26-C21-P2 | 117.9(4) |
| C27-P1-C39 | 108.80(19) | C2-C3-C8 | 117.0(7) | C23-C22-C21 | 120.5(6) |
| C33-P1-C39 | 104.8(2) | C8'-C3-C4' | 115.8(8) | C24-C23-C22 | 121.3(6) |
| C27-P1-Au1 | 111.98(15) | C4-C3-C4' | 28.5(5) | C23-C24-C25 | 119.7(6) |
| C33-P1-Au1 | 114.18(14) | C2-C3-C4' | 118.4(5) | C24-C25-C26 | 119.4(6) |
| C39-P1-Au1 | 111.97(15) | C8'-C3-C4' | 121.5(8) | C25-C26-C21 | 121.8(5) |
| C15-P2-C21 | 107.6(2) | C3-C4-C5 | 124.1(9) | C32'-C27-C28 | 107.2(9) |
| C15-P2-C9 | 105.5(2) | C4-C5-C6 | 119.9(11) | C32'-C27-C28' | 119.3(9) |
| C21-P2-C9 | 105.0(2) | C5-C6-C7 | 116.9(11) | C39-C40-C41 | 120.4(4) |
| C15-P2-Au2 | 112.77(16) | C8-C7-C6 | 122.4(13) | C42-C41-C40 | 120.8(5) |
| C21-P2-Au2 | 112.54(18) | C7-C8-C3 | 119.5(13) | C41-C42-C43 | 119.3(4) |
| C9-P2-Au2 | 112.88(15) | C5'-C4'-C3 | 120.1(9) | C42-C43-C44 | 120.2(5) |
| N2-N3-C2 | 107.9(4) | C6'-C5'-C4' | 121.5(11) | C43-C44-C39 | 120.2(5) |
| N2-N1-C1 | 110.7(3) | C5'-C6'-C7' | 120.6(12) | C46-C45-C50 | 119.5(7) |
| N2-N1-Au1 | 126.0(3) | C6'-C7'-C8' | 120.0(12) | C47-C46-C45 | 121.7(7) |
| C1-N1-Au1 | 122.8(3) | C3-C8'-C7' | 121.6(12) | C46-C47-C48 | 119.9(6) |
| N3-N2-N1 | 108.0(4) | C14-C9-C10 | 119.1(5) | C47-C48-C49 | 118.8(6) |
| N1-C1-C2 | 104.1(4) | C14-C9-P2 | 117.9(4) | C50-C49-C48 | 118.7(6) |
| N1-C1-Au2 | 120.2(3) | C10-C9-P2 | 123.0(4) | C49-C50-C45 | 121.4(6) |
| C2-C1-Au2 | 135.6(3) | C11-C10-C9 | 119.7(5) | C52-C51-C56 | 120.0(8) |
| N3-C2-C1 | 109.3(4) | C12-C11-C10 | 120.5(5) | C27-C32'-C31' | 120.8(13) |
| N3-C2-C3 | 121.0(4) | C13-C12-C11 | 120.5(6) | C38-C33-C34 | 119.2(4) |
| C1-C2-C3 | 129.6(4) | C12-C13-C14 | 119.4(5) | C38-C33-P1 | 117.9(3) |
| C8'-C3-C4 | 105.0(8) | C9-C14-C13 | 120.8(5) | C34-C33-P1 | 122.9(3) |
| C8'-C3-C2 | 125.4(7) | C20'-C15-C16 | 122.9(8) | C35-C34-C33 | 120.0(4) |
| C20'-C15-C20 | 10.0(12) | C28-C27-C28' | 25.9(6) | C36-C35-C34 | 120.2(5) |
| C16-C15-C20 | 120.0(6) | C32'-C27-C32 | 16.8(8) | C37-C36-C35 | 120.4(5) |
| C20'-C15-C16' | 114.9(11) | C28-C27-C32 | 117.0(8) | C36-C37-C38 | 120.3(5) |
| C16-C15-C16' | 18.4(9) | C28'-C27-C32 | 121.8(7) | C37-C38-C33 | 120.0(4) |
| C20-C15-C16' | 109.2(7) | C32'-C27-P1 | 121.6(7) | C40-C39-C44 | 119.0(4) |
| C20'-C15-P2 | 117.9(8) | C28-C27-P1 | 127.1(6) | C40-C39-P1 | 121.9(3) |
| C16-C15-P2 | 119.0(4) | C28'-C27-P1 | 119.1(6) | C44-C39-P1 | 118.8(4) |
| C20-C15-P2 | 120.7(4) | C32-C27-P1 | 115.4(6) | C53-C52-C51 | 120.0(7) |
| C16'-C15-P2 | 125.7(7) | C27-C28-C29 | 122.7(9) | C52-C53-C54 | 120.0(8) |
| C15-C16-C17 | 120.(7) | C30-C29-C28 | 118.0(9) | C53-C54-C55 | 120.0(8) |
| C18-C17-C16 | 120.0(9) | C31-C30-C29 | 120.1(10) | C54-C55-C56 | 120.0(8) |
| C19-C18-C17 | 120.0(9) | C32-C31-C30 | 121.7(11) | C55-C56-C51 | 120.1(8) |
| C18-C19-C20 | 120.0(9) | C31-C32-C27 | 120(1) | C52'-C51'-C56' | 120.0(6) |
| C19-C20-C15 | 120.0(8) | C29'-C28'-C27 | 118.7(10) | C51'-C52'-C53' | 120.0(6) |
| C17'-C16'-C15 | 120.8(13) | C30'-C29'-C28' | 122.0(12) | C54'-C53'-C52' | 120.0(6) |
| C18'-C17'-C16' | 118.5(13) | C29'-C30'-C31' | 119.4(14) | C55'-C54'-C53' | 120.0(6) |

TABLE 3-continued

Bond angles (°) for $3_{1,5}$.

| Bond | Angle | Bond | Angle | Bond | Angle |
|---|---|---|---|---|---|
| C17'-C18'-C19' | 121.5(14) | C30'-C31'-C32' | 119.7(14) | C56'-C55'-C54' | 120.0(6) |
| C18'-C19'-C20' | 118.4(15) | C15-C20'-C19' | 125.4(15) | C55'-C56'-C51' | 120.0(6) |

TABLE 4

Anisotropic displacement parameters ($Å^2 \times 10^3$) for $3_{(1,5)}$. The anisotropic displacement factor exponent takes the form: $-2\pi^2[h^2 a^{*2} U^{11} + \ldots + 2 h k a^* b^* U^{12}]$.

| | U11 | U22 | U33 | U23 | U13 | U12 |
|---|---|---|---|---|---|---|
| Au1 | 19(1) | 22(1) | 17(1) | 0(1) | −1(1) | 2(1) |
| Au2 | 22(1) | 21(1) | 19(1) | −1(1) | 2(1) | 5(1) |
| P1 | 19(1) | 20(1) | 19(1) | 0(1) | 0(1) | 1(1) |
| P2 | 32(1) | 27(1) | 24(1) | 2(1) | 6(1) | 12(1) |
| N1 | 22(2) | 21(2) | 18(2) | 1(2) | 0(2) | 4(2) |
| N2 | 29(2) | 36(3) | 19(2) | −4(2) | 4(2) | 8(2) |
| N3 | 25(2) | 31(3) | 29(3) | 0(2) | 0(2) | 4(2) |
| C1 | 17(2) | 20(3) | 16(2) | −4(2) | −2(2) | −2(2) |
| C2 | 17(2) | 26(3) | 20(3) | −3(2) | 1(2) | −3(2) |
| C3 | 17(2) | 27(3) | 31(3) | 4(2) | −2(2) | 2(2) |
| C9 | 34(3) | 24(3) | 22(3) | −4(2) | 11(2) | 5(2) |
| C10 | 41(3) | 62(4) | 28(3) | 3(3) | 7(2) | 10(3) |
| C11 | 43(4) | 85(5) | 35(4) | 7(3) | 16(3) | −2(3) |
| C12 | 64(4) | 64(4) | 25(3) | 9(3) | 4(3) | −13(3) |
| C13 | 47(3) | 42(3) | 25(3) | 3(3) | 2(2) | −4(3) |
| C14 | 34(3) | 31(3) | 27(3) | −1(2) | 1(2) | −1(2) |
| C15 | 40(3) | 30(3) | 43(3) | −2(3) | 0(3) | 16(2) |
| C21 | 32(3) | 45(3) | 25(3) | 9(3) | 4(2) | 13(2) |
| C22 | 60(4) | 68(5) | 56(5) | −14(4) | −11(3) | 38(3) |
| C23 | 58(5) | 100(6) | 66(5) | −2(5) | −21(4) | 43(4) |
| C24 | 29(3) | 111(6) | 32(4) | 17(4) | −2(3) | 8(4) |
| C25 | 32(3) | 66(4) | 47(4) | 1(3) | 3(3) | 0(3) |
| C26 | 26(3) | 54(4) | 46(4) | 0(3) | −1(3) | 10(3) |
| C27 | 22(2) | 24(3) | 17(3) | 3(2) | −1(2) | 3(2) |
| C33 | 19(2) | 23(3) | 15(2) | −3(2) | −4(2) | −4(2) |
| C34 | 24(3) | 25(3) | 23(3) | 0(2) | 0(2) | 1(2) |
| C35 | 32(3) | 29(3) | 25(3) | 4(2) | −2(2) | −5(2) |
| C36 | 27(3) | 42(3) | 30(3) | 5(3) | 2(2) | −11(2) |
| C37 | 24(3) | 36(3) | 34(3) | −4(3) | 3(2) | −1(2) |
| C38 | 20(2) | 26(3) | 28(3) | 2(2) | −6(2) | −5(2) |
| C39 | 20(2) | 17(2) | 23(3) | −2(2) | 1(2) | 2(2) |
| C40 | 20(2) | 29(3) | 20(3) | 5(2) | 0(2) | −3(2) |
| C41 | 23(2) | 41(3) | 26(3) | 0(3) | −3(2) | −1(2) |
| C42 | 22(3) | 33(3) | 32(3) | −3(3) | −6(2) | −6(2) |
| C43 | 37(3) | 41(3) | 36(3) | 10(3) | −5(3) | −18(3) |
| C44 | 39(3) | 43(3) | 26(3) | 10(3) | −8(2) | −14(3) |
| C45 | 56(4) | 47(4) | 68(5) | −2(4) | 14(3) | −14(3) |
| C46 | 55(4) | 41(4) | 78(6) | 15(4) | 2(4) | −7(3) |
| C47 | 45(4) | 33(4) | 98(6) | −4(4) | 15(4) | 9(3) |
| C48 | 71(5) | 68(5) | 58(5) | −13(4) | 20(4) | −10(4) |
| C49 | 59(4) | 48(4) | 65(5) | 16(4) | −17(4) | 5(3) |
| C50 | 31(3) | 45(4) | 80(6) | −17(4) | 6(3) | 5(3) |

Computational Results for $3_{1,5}$.

TABLE 5

Optimized Cartesian coordinates of ground-state (singlet) for $3_{1,5}$.

| Atom | x | y | z |
|---|---|---|---|
| Au | 3.13414 | −0.50824 | −0.12262 |
| Au | −3.1182 | −0.53687 | 0.00241 |
| P | 5.42199 | −0.15626 | 0.03395 |
| P | −5.4768 | −0.14276 | 0.01235 |
| N | −0.61742 | −2.20306 | −0.14505 |
| N | 1.09665 | −0.87802 | −0.21797 |
| N | 0.69437 | −2.17095 | −0.22824 |
| C | 0.00288 | −0.06645 | −0.10413 |
| C | −1.10297 | −0.92136 | −0.05757 |
| C | 0.09247 | 1.39864 | −0.06948 |
| C | 0.95307 | 2.10346 | −0.93354 |
| C | 1.03565 | 3.49634 | −0.88894 |
| C | 0.25346 | 4.22122 | 0.0136 |
| C | −0.61287 | 3.53672 | 0.87043 |
| C | −0.68992 | 2.14434 | 0.83298 |
| C | −5.91906 | 1.64342 | 0.01789 |
| C | −7.04495 | 2.15246 | 0.68227 |
| C | −7.33119 | 3.51873 | 0.63698 |
| C | −6.49876 | 4.38745 | −0.07097 |
| C | −5.37225 | 3.88908 | −0.7297 |
| C | −5.07873 | 2.52632 | −0.68116 |
| C | −6.32574 | −0.84244 | −1.46235 |
| C | −7.46026 | −0.25348 | −2.04098 |
| C | −8.06834 | −0.84089 | −3.15225 |
| C | −7.55017 | −2.01851 | −3.69487 |
| C | −6.41668 | −2.60632 | −3.12886 |
| C | −5.80222 | −2.01972 | −2.0222 |
| C | −6.35486 | −0.86439 | 1.4596 |
| C | −7.67905 | −1.3248 | 1.39691 |
| C | −8.29609 | −1.85073 | 2.53359 |
| C | −7.59838 | −1.92331 | 3.74087 |
| C | −6.27752 | −1.4749 | 3.80933 |
| C | −5.65567 | −0.95371 | 2.67445 |
| C | 5.88167 | 1.61643 | −0.09362 |
| C | 7.11208 | 2.03318 | −0.62514 |
| C | 7.42779 | 3.39183 | −0.68134 |
| C | 6.52032 | 4.34304 | −0.2105 |
| C | 5.29125 | 3.93521 | 0.31247 |
| C | 4.96893 | 2.57899 | 0.36766 |
| C | 6.11015 | −0.74971 | 1.62962 |
| C | 7.18882 | −0.11658 | 2.26506 |
| C | 7.69091 | −0.62316 | 3.46548 |
| C | 7.12198 | −1.76176 | 4.03903 |
| C | 6.04354 | −2.39273 | 3.41448 |
| C | 5.53429 | −1.88791 | 2.2182 |
| C | 6.37937 | −1.01757 | −1.2754 |
| C | 7.66141 | −1.54001 | −1.04726 |
| C | 8.35813 | −2.1665 | −2.08254 |
| C | 7.78291 | −2.27718 | −3.34966 |
| C | 6.50422 | −1.76513 | −3.58159 |
| C | 5.80208 | −1.1431 | −2.54968 |
| H | 1.53634 | 1.55049 | −1.6648 |
| H | 1.70148 | 4.01637 | −1.57409 |
| H | 0.31409 | 5.30632 | 0.04552 |
| H | −1.22478 | 4.08839 | 1.58033 |
| H | −1.34892 | 1.61425 | 1.51396 |
| H | −7.69305 | 1.48654 | 1.24408 |
| H | −8.2039 | 3.90273 | 1.15863 |
| H | −6.72217 | 5.45055 | −0.10224 |
| H | −4.71282 | 4.56127 | −1.2716 |
| H | −4.18823 | 2.14547 | −1.17465 |
| H | −7.86233 | 0.66931 | −1.63301 |
| H | −8.9442 | −0.37462 | −3.5957 |
| H | −8.02297 | −2.47179 | −4.56206 |
| H | −6.00094 | −3.5152 | −3.55474 |
| H | −4.90622 | −2.4667 | −1.5988 |
| H | −8.22515 | −1.28579 | 0.45903 |
| H | −9.32047 | −2.20857 | 2.47283 |
| H | −8.07917 | −2.33751 | 4.62306 |
| H | −5.72478 | −1.54246 | 4.74225 |
| H | −4.61968 | −0.62825 | 2.72318 |
| H | 7.81799 | 1.30128 | −1.00644 |

TABLE 5-continued

Optimized Cartesian coordinates of ground-state (singlet) for $3_{1,5}$.

| Atom | x | y | z |
|---|---|---|---|
| H | 8.38083 | 3.70563 | −1.09838 |
| H | 6.76683 | 5.40019 | −0.25973 |
| H | 4.57413 | 4.67014 | 0.66661 |
| H | 4.00144 | 2.2693 | 0.75343 |
| H | 7.62925 | 0.77659 | 1.83217 |
| H | 8.52326 | −0.12343 | 3.95347 |
| H | 7.51192 | −2.15151 | 4.97534 |
| H | 5.58885 | −3.27151 | 3.86266 |
| H | 4.68199 | −2.37033 | 1.74639 |
| H | 8.11183 | −1.47102 | −0.06167 |
| H | 9.3483 | −2.57272 | −1.89495 |
| H | 8.3252 | −2.76995 | −4.15194 |
| H | 6.04589 | −1.86095 | −4.56174 |
| H | 4.79843 | −0.76625 | −2.72856 |

Computational Results for $3_{1,4}$.

TABLE 6

Optimized Cartesian coordinates of ground-state (singlet) for $3_{1,4}$.

| Atom | x | y | z |
|---|---|---|---|
| Au | −1.82905 | 1.43078 | −0.00219 |
| Au | 1.80779 | 0.57941 | −0.01463 |
| P | −3.64515 | −0.01271 | −0.02323 |
| P | 2.67095 | −1.64619 | 0.03194 |
| N | 0.66983 | 4.71031 | 0.03241 |
| N | −0.25841 | 2.76217 | 0.00994 |
| N | −0.488 | 4.10199 | 0.04587 |
| C | 1.08321 | 2.50081 | −0.03233 |
| C | 1.66763 | 3.77544 | −0.02028 |
| C | 3.07652 | 4.19284 | −0.041 |
| C | 4.1148 | 3.32287 | −0.42138 |
| C | 5.44403 | 3.74601 | −0.42721 |
| C | 5.77158 | 5.0539 | −0.06228 |
| C | 4.74874 | 5.93288 | 0.30498 |
| C | 3.42113 | 5.51019 | 0.31626 |
| C | 4.50421 | −1.69995 | 0.15092 |
| C | 5.27954 | −2.69228 | −0.46774 |
| C | 6.66901 | −2.68684 | −0.3285 |
| C | 7.2948 | −1.69385 | 0.42761 |
| C | 6.52977 | −0.69946 | 1.04164 |
| C | 5.14198 | −0.69716 | 0.90056 |
| C | 2.06152 | −2.65286 | 1.44506 |
| C | 2.82407 | −3.67318 | 2.03472 |
| C | 2.30272 | −4.41835 | 3.094 |
| C | 1.01878 | −4.15238 | 3.5745 |
| C | 0.25681 | −3.13279 | 2.99973 |
| C | 0.77702 | −2.38223 | 1.9448 |
| C | 2.25686 | −2.62159 | −1.47466 |
| C | 1.99567 | −3.9997 | −1.44581 |
| C | 1.6991 | −4.68572 | −2.62579 |
| C | 1.6622 | −4.00425 | −3.84419 |
| C | 1.9143 | −2.62984 | −3.88052 |
| C | 2.2033 | −1.94001 | −2.70249 |
| C | −3.76769 | −1.04331 | 1.49495 |
| C | −4.24013 | −2.36394 | 1.47533 |
| C | −4.337 | −3.09353 | 2.6624 |
| C | −3.96546 | −2.51205 | 3.87628 |
| C | −3.48846 | −1.19838 | 3.90239 |
| C | −3.38389 | −0.46813 | 2.71818 |
| C | −5.24227 | 0.88438 | −0.13682 |
| C | −6.42828 | 0.37446 | 0.41409 |
| C | −7.62381 | 1.08287 | 0.28255 |
| C | −7.64473 | 2.30342 | −0.39564 |
| C | −6.46652 | 2.82029 | −0.93858 |
| C | −5.26797 | 2.1185 | −0.80713 |
| C | −3.61676 | −1.19425 | −1.42861 |
| C | −4.78912 | −1.68816 | −2.021 |
| C | −4.71137 | −2.60508 | −3.0709 |
| C | −3.46716 | −3.0346 | −3.53713 |

TABLE 6-continued

Optimized Cartesian coordinates of ground-state (singlet) for $3_{1,4}$.

| Atom | x | y | z |
|---|---|---|---|
| C | −2.29585 | −2.54062 | −2.95837 |
| C | −2.36889 | −1.6201 | −1.91269 |
| H | 3.86991 | 2.3092 | −0.72856 |
| H | 6.22563 | 3.05225 | −0.73031 |
| H | 6.80712 | 5.38534 | −0.07066 |
| H | 4.98703 | 6.95614 | 0.58689 |
| H | 2.62465 | 6.1905 | 0.59912 |
| H | 4.80264 | −3.46168 | −1.06769 |
| H | 7.26132 | −3.45699 | −0.8153 |
| H | 8.37651 | −1.68941 | 0.53057 |
| H | 7.01138 | 0.084 | 1.61971 |
| H | 4.55335 | 0.09176 | 1.3618 |
| H | 3.82895 | −3.87839 | 1.67751 |
| H | 2.90348 | −5.20264 | 3.54667 |
| H | 0.61775 | −4.73163 | 4.40193 |
| H | −0.73775 | −2.91075 | 3.37638 |
| H | 0.19166 | −1.5723 | 1.51737 |
| H | 2.01448 | −4.53749 | −0.50279 |
| H | 1.4974 | −5.753 | −2.59102 |
| H | 1.43574 | −4.54077 | −4.76178 |
| H | 1.88034 | −2.0919 | −4.82386 |
| H | 2.37954 | −0.86767 | −2.73202 |
| H | −4.52351 | −2.82748 | 0.53526 |
| H | −4.70171 | −4.11675 | 2.63611 |
| H | −4.04383 | −3.08086 | 4.79886 |
| H | −3.19151 | −0.74233 | 4.84261 |
| H | −2.99761 | 0.54778 | 2.74079 |
| H | −6.41783 | −0.56579 | 0.95766 |
| H | −8.53651 | 0.68327 | 0.71609 |
| H | −8.57547 | 2.85579 | −0.49148 |
| H | −6.47411 | 3.7767 | −1.4533 |
| H | −4.34885 | 2.53606 | −1.20994 |
| H | −5.76069 | −1.34895 | −1.67444 |
| H | −5.62411 | −2.97785 | −3.52768 |
| H | −3.41093 | −3.745 | −4.3575 |
| H | −1.32411 | −2.8597 | −3.32432 |
| H | −1.45576 | −1.21808 | −1.48139 |

Synthesis of Substituted Homo-bimetallic Complexes

Homo-bimetallic complexes with different R groups were substituted on the acetylide group and used in the iClick reaction as shown in Scheme 9, below.

Scheme 9

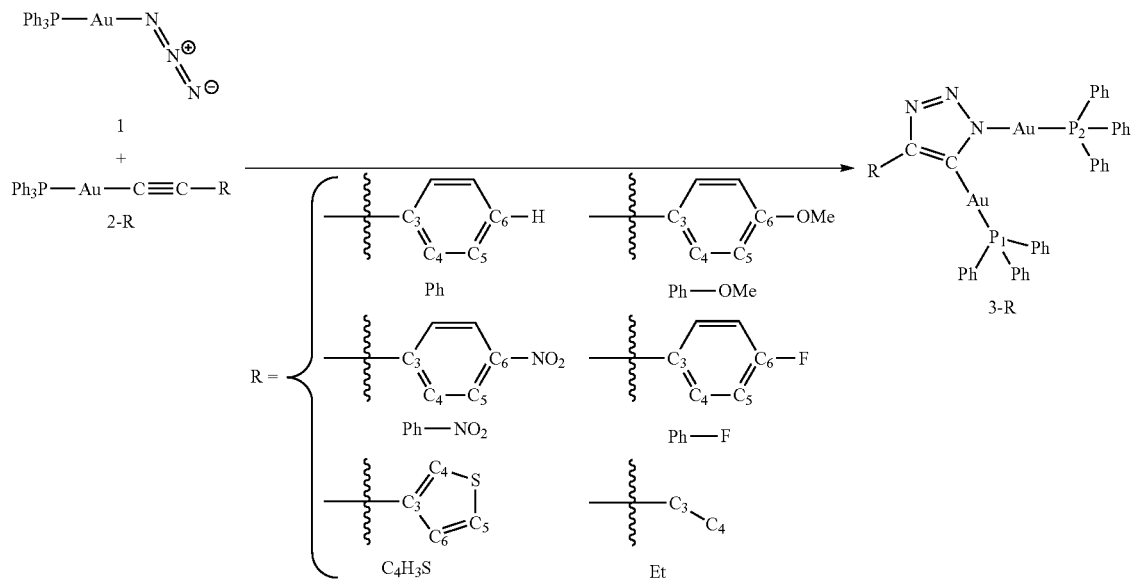

Synthesis of 3-R(R═OMe, NO₂, F)

Figure 11:
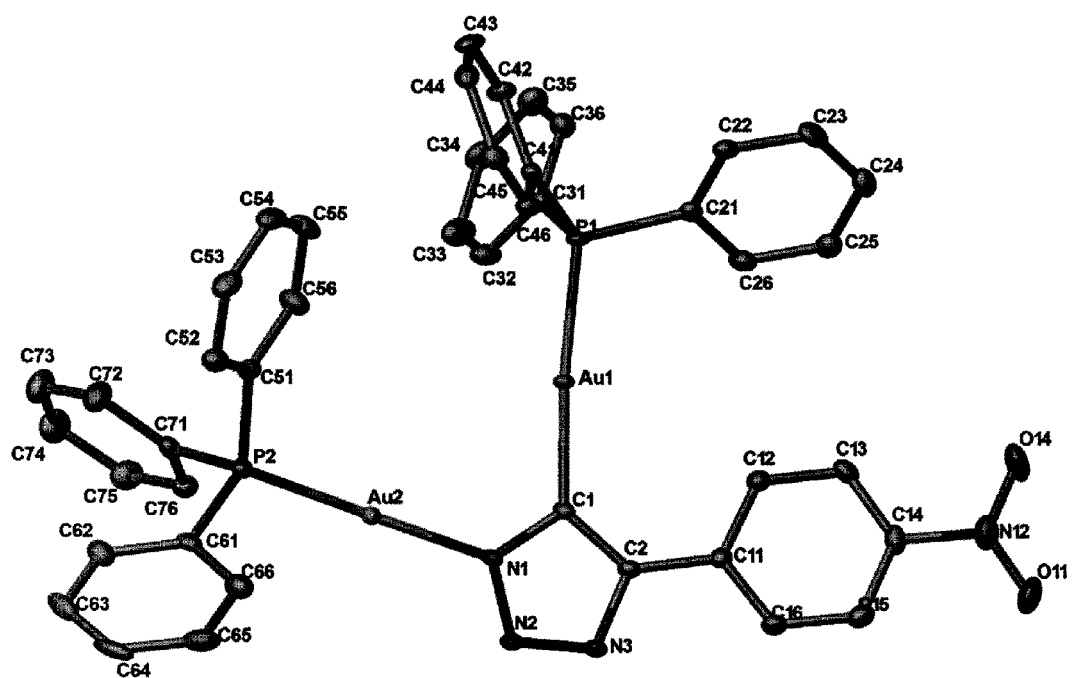
FIG. 11 shows the molecular structure of complex of 3-NO$_2$, according to an embodiment of the invention, as determined by single crystal X-ray diffraction experiments.

PPh₃-Au—N₃ ((1) 12.4 mg, 0.0248 mmol) and PPh₃-Au—C≡C—C₆H₄—R ((2-R) 0.0248 mmol) were combined in a vial, to which 0.6 ml chloroform-d was added. The solution was transferred to an NMR tube, and reaction was monitored via NMR. Complete reaction was indicated by disappearance of $^1$H and $^{31}$P NMR resonances of the starting materials, Fluorine NMR was carried out for the 3-F preparation. For 3-OMe, resonances attributable to the methyl protons on the methoxy group was easily monitored. All 3-Rs display two slightly broadened signals in the $^{31}$P[{$^1$H}] NMR spectra that is very similar from compound to compound. The products, with the exception of 3-NO₂, were not isolated. 3-NO₂ was isolated by removing solvent in vacuo, dissolving the residue in a minimal amount of methylene chloride, and precipitating the product as a bright yellow solid, from pentane. Single crystals were grown by addition of pentane to a methylene chloride solution of 3-NO₂. The molecular structure for 3-NO₂ from x-ray data is shown in FIG. 11.

Synthesis of 3-Et

PPh₃-Au—N₃ (17.0 mg, 0.0339 mmol) and PPh₃-Au—C≡C-Et (17.4 mg, 0.0039 mmol) were combined in a vial, to which 0.6 ml chloroform-d was added. The solution was transferred to an NMR tube, and the reaction was monitored via NMR. The reaction appeared to be complete within one hour, with the emergence of two resonances for the ethyl substituent (a quartet at 2.96 ppm, and a triplet at 1.42 ppm) and the disappearances of the resonances attributable to the ethyl substituent in the starting material (a quartet at 2.39 ppm and a triplet at 1.21 ppm). The product (3-Et) was isolated in 93% yield.

Synthesis of 3-C₄H₃S

PPh₃-Au—N₃ (63.0 mg, 0.111 mmol) and PPh₃-Au—C≡C—C₄H₃S (55.8 mg, 0.111 mmol) were combined in a vial, to which 8 ml methylene chloride was added. The solution was stirred for 2 hours, and the solvent volume was reduced in vacuo. about 5 ml hexane was added to the concentrated solution to precipitate the colorless product.

TABLE 7

Selected notable NMR resonances for iClick reactions with substituted acetylenes.

| R | H3 | H4 | H5 | H6 | R | P1 | P2 |
|---|---|---|---|---|---|---|---|
| Ph—OMe | — | 8.3 (d, $^3J_{HH}=$ 8.21 Hz) | 6.85 (d, $^3J_{HH}=$ 8.78 Hz) | — | OCH₃: 3.82 (s) | 45.19 (s) | 32.66 (s) |
| Ph—NO₂ | — | 8.60 (d, $^3J_{HH}=$ 8.5 Hz) | 8.12 (d, $^3J_{HH}=$ 8.8 Hz) | — | — | 44.98 (s) | 32.30 (s) |
| Ph—F | — | 8.34 (d, $^3J_{HH}=$ 8.78 Hz) | 8.32 (d, $^3J_{HH}=$ 8.78 Hz) | — | F: −118.83 (s) | 45.2 (s) | 32.74 (s) |
| C₄H₃S | — | 7.17 (s) | 7.97 (d, $^3J_{HH}=$ 4.53 Hz) | 7.90 (d, $^3J_{HH}=$ 3.68 Hz) | — | 45.80 (s) | 32.44 (s) |
| Et | 2.96 (q, $^3J_{HH}=$ 7.64 Hz) | 1.42 (t, $^3J_{HH}=$ 7.64 Hz) | — | — | — | 45.55 (s) | 31.77 (s) |

X-Ray experimental for 3-NO$_2$: X-Ray Intensity data were collected at 100K on a Bruker SMART diffractometer using MoKα radiation (λ=0.71073 Å) and an APEXII CCD area detector.

Raw data frames were read by program SAINT[1] and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces.

The structure was solved and refined in SHELXTL6.1, using full-matrix least-squares refinement. The non-H atoms were refined with anisotropic thermal parameters and all of the H atoms were calculated in idealized positions and refined riding on their parent atoms. There are two chloroform solvent molecules in the asymmetric unit, one of which is partially disordered where only two of the Cl atoms are disordered. In this case, atom C81 should also be disordered but it is to a lesser extent which did not allow for its resolution. In the final cycle of refinement, 10806 reflections (of which 9294 are observed with I>2σ(I)) were used to refine 570 parameters and the resulting R$_1$, wR$_2$ and S (goodness of fit) were 2.13%, 4.96% and 0.981, respectively. The refinement was carried out by minimizing the wR$_2$ function using F$^2$ rather than F values. R$_1$ is calculated to provide a reference to the conventional R value but its function is not minimized.

TABLE 8

Crystal data and structure refinement for 1-NO$_2$.

| | |
|---|---|
| Identification code | apow6 |
| Empirical formula | C46 H36 Au2 Cl6 N4 O2 P2 |
| Formula weight | 1345.36 |
| Temperature | 100(2) K |
| Wavelength | 0.71073 Å |
| Crystal system | Triclinic |
| Space group | P$\bar{1}$ |
| Unit cell dimensions | a = 13.1709(4) Å  α = 104.570(2)°. |
| | b = 13.9693(4) Å  β = 113.005(1)°. |
| | c = 15.1962(4) Å  γ = 101.240(2)°. |
| Volume | 2352.00(12) Å$^3$ |
| Z | 2 |
| Density (calculated) | 1.900 Mg/m$^3$ |
| Absorption coefficient | 6.682 mm$^{-1}$ |
| F(000) | 1292 |
| Crystal size | 0.35 × 0.06 × 0.05 mm$^3$ |
| Theta range for data collection | 1.56 to 27.50°. |
| Index ranges | −17 ≤ h ≤ 17, −18 ≤ k ≤ 18, −19 ≤ l ≤ 19 |
| Reflections collected | 79139 |
| Independent reflections | 10806 [R(int) = 0.0712] |
| Completeness to theta = 27.50° | 100.0% |
| Absorption correction | Integration |
| Max. and min. transmission | 0.7142 and 0.2013 |
| Refinement method | Full-matrix least-squares on F$^2$ |
| Data/restraints/parameters | 10806/0/570 |
| Goodness-of-fit on F$^2$ | 0.981 |
| Final R indices [I > 2sigma(I)] | R1 = 0.0213, wR2 = 0.0496 [9294] |
| R indices (all data) | R1 = 0.0274, wR2 = 0.0515 |
| Largest diff. peak and hole | 1.577 and −1.305 e.Å$^{-3}$ |

R1 = Σ(||F$_o$| − |F$_c$||)/Σ|F$_o$|
wR2 = [Σ[w(F$_o$$^2$ − F$_c$$^2$)$^2$]/Σ[w(F$_o$$^2$)$^2$]]$^{1/2}$
S = [Σ[w(F$_o$$^2$ − F$_c$$^2$)$^2$]/(n-p)]$^{1/2}$
w = 1/[σ$^2$(F$_o$$^2$) + (m*p)$^2$ + n*p], p = [max(F$_o$$^2$, 0) + 2* Fc$^2$]/3, m & n are constants.

Synthesis and Characterization of 5-NO$_2$.

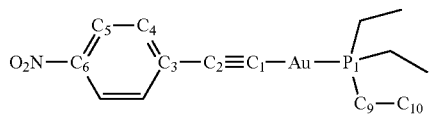

To a 2-neck round bottom flask charged with a magnetic stirbar, was added chlorotriethylphosphine gold(I) (100 mg, 0.285 mmol), and 1-ethynyl-4-nitrobenzene (50.4 mg, 0.342 mmol). The flask was evacuated and then filled with argon and 5 mL of dry methanol was added via syringe. 10 mL of a freshly prepared 0.262 M solution of sodium methoxide in methanol (made from 60 mg (2.62 mmol) sodium metal in 10 mL dry methanol) was added via syringe. The suspension was allowed to stir under argon for 16 h. The following workup was done with no precaution to exclude air and water. The solution volume was reduced in vacuo to approximately 5 mL, at which time the yellow suspension was filtered through a glass fitted funnel, and the solid material was washed with cold methanol and pentane. The solid material was then taken up in chloroform, allowed to stir for 1 h and then all volatiles were removed in vacuo, and the residue triturated with pentane. The $^{31}$P{$^1$H} NMR reveals two resonances in the spectra of the initial solid material (39.96 and 37.92 ppm), which upon sitting in chloroform all product converts to a single product (37.92 ppm)). 77% Yield (101 mg, 0.219 mmol). $^1$H NMR (500 MHz, CDCl$_3$): δ 8.10 (d, $^3$J$_{HH}$=8.6 Hz, 2H, H5), 7.56 (d, $^3$J$_{HH}$=8.6 Hz, 2H, H4), 1.84 (dq, $^2$J$_{PH}$=7.6 Hz, $^3$J$_{HH}$=7.7 Hz, 6H, H9), 1.22 (dt, $^3$J$_{PH}$=18.2 Hz, $^3$J$_{HH}$=7.7 Hz, 9H, H10). $^{13}$C NMR Shifts (indirect detection through $^1$H-$^{13}$C gHMBC and $^1$H-$^{13}$C gHSQC (500 MHz, CDCl$_3$)): δ 145.8 (C6), 132.8 (C4), 132.5 (C3), 123.4 (C5), 102.3 (C2), 17.8 (C9), 8.9 (C10) (Note: C$_1$ is not observed). $^{31}$P{$^1$H} NMR (121.4 MHz, CDCl$_3$): δ 37.92 (s, P1). Anal. Calcd for C$_{14}$H$_{19}$AuNO$_2$: C, 36.46; H, 4.15; N, 3.04. Found: C, 36.48; H, 4.13; N, 3.00.

Synthesis and Characterization of cis-6-Ph.

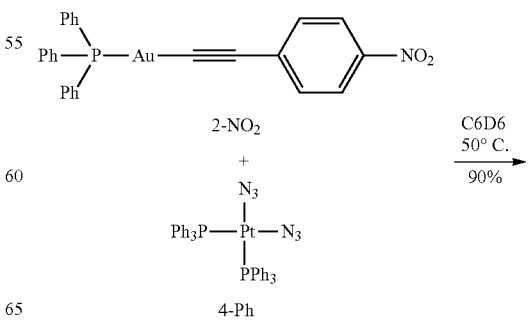

-continued

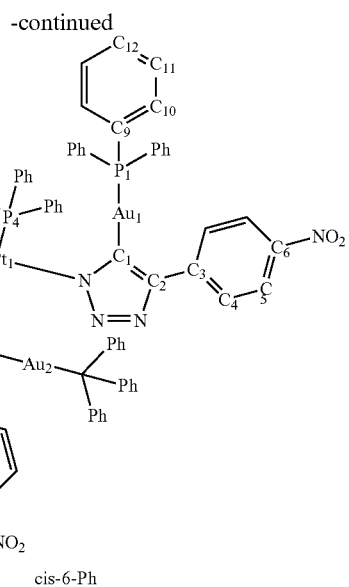

cis-6-Ph

Figure 7:
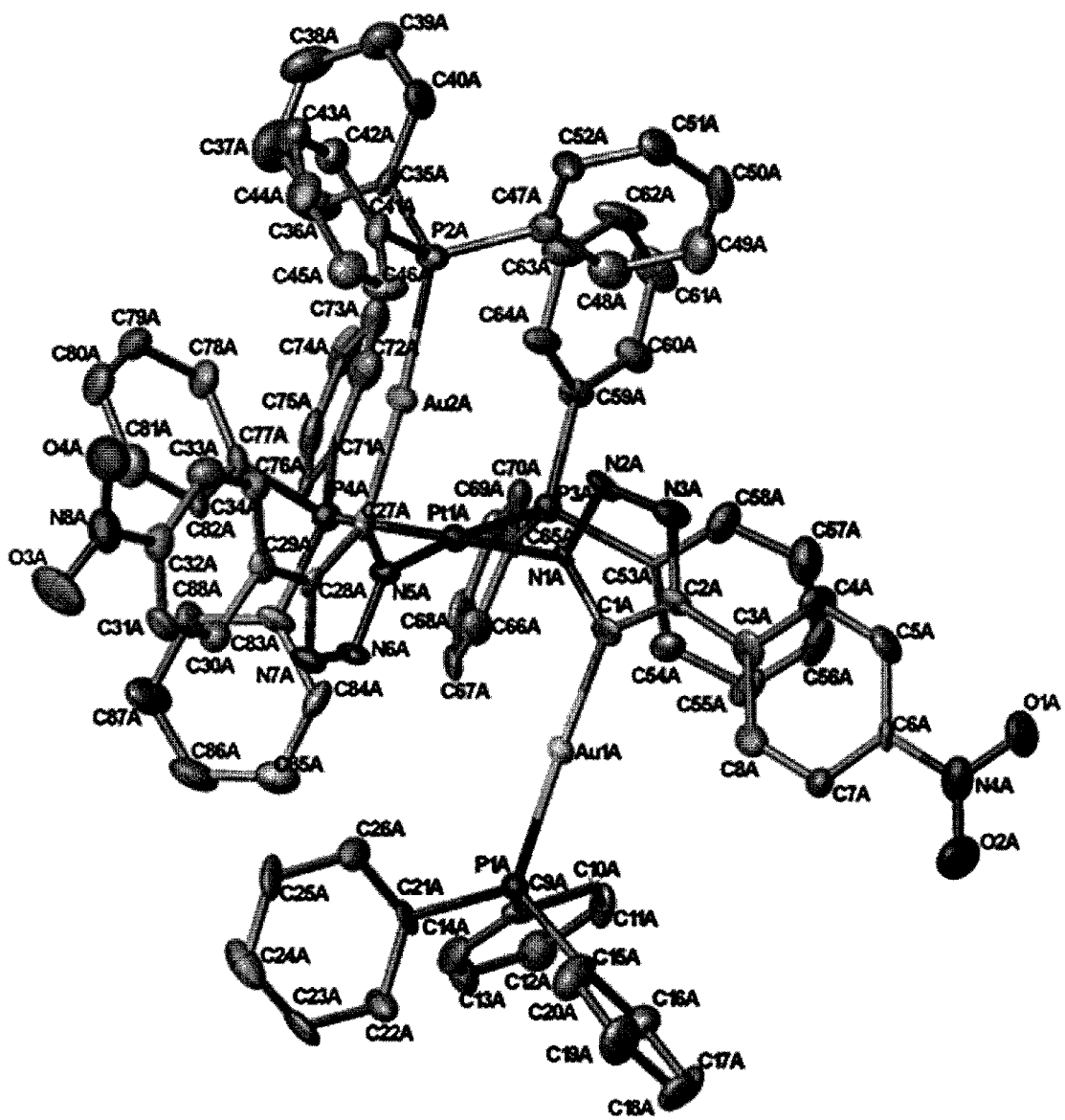
FIG. 7 shows the molecular structure of complex of cis-6-Ph, according to an embodiment of the invention, as determined by single crystal X-ray diffraction experiments.

To a vial containing cis-(PPh$_3$)$_2$Pt(N$_3$)$_2$ (4-Ph) (15.5 mg, 0.0193 mmol) and PPh$_3$Au$^I$C≡CC$_6$H$_4$NO$_2$) (2-NO$_2$) (23.4 mg, 0.0386 mmol), was added 0.6 ml C$_6$D$_6$. The suspension of the sparingly soluble platinum complex and the soluble gold complex in benzene, was transferred to a sealable J. Young NMR tube, with an additional 0.2 ml of C$_6$D$_6$. The NMR tube was sealed and the mixture degased by a freeze-pump-thaw cycle. The reaction vessel was heated to 50° C. and maintained for 3.5 hours. All material dissolved within 10 minutes, and within an additional 20 minutes, large amounts of yellow crystalline solid had formed on the walls of the tube. After 3.5 hours the sample was slowly cooled to room temperature, where additional product crystallized overnight. A yellow crystalline solid was isolated by decanting the supernatant and washing with pentane to provide analytically pure cis-6-Ph in 90% yield (35.1 mg, 0.0174 mmol). NMR $^1$H (300 MHz, CDCl$_3$): δ 8.04 (d, $^3J_{HH}$=8.7 Hz, 4H, H4), 7.95 (m, 12H, H10), 7.83 (d, $^3J_{HH}$=9.0 Hz, 4H, H5), 7.60 (m, 18H, H11/H12), 7.46 (t, $^3J_{HH}$=8.8 Hz, 12H, H54), 7.06 (t, $^3J_{HH}$=8.8 Hz, 6H, H56), 6.73 (t, $^3J_{HH}$=7.2 Hz, 6H, H55). $^{13}$C NMR Shifts (indirect detection through $^1$H-$^{13}$C gHMBC and $^1$H-$^{13}$C gHSQC (500 MHz, CDCl$_3$)): δ 151.5 (C2), 144.4 (C3), 144.2 (C6), 134.9 (C10), 134.7 (C54), 131.6 (C9), 131.2 (C12), 129.8 (C56), 129.3 (C11), 128.4 (C53), 127.5 (C55), 125.5 (C4), 123.1 (C5). NMR $^{31}$P (121.4 MHz, CDCl$_3$): δ 43.53 (s, (P1)), 7.79 (s, w/satellites: $^1J_{Pt-P}$=3095 Hz, (P3)). Anal. Calcd for C$_{88}$H$_{68}$Au$_2$N$_8$O$_4$P$_4$Pt: C, 52.47; H, 3.40; N, 5.56. Found: C, 52.38; H, 3.48; N, 5.71. The molecular structure for cis-6-Ph from x-ray data is shown in FIG. 7. X-Ray experimental for cis 6-Ph: X-Ray Intensity data were collected at 100K on a Bruker DUO diffractometer using MoKα radiation (λ=0.71073 Å) and an APEXII CCD area detector.

Raw data frames were read by program SAINT$^1$ and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces.

The structure was solved and refined in SHELXTL6.1, using full-matrix least-squares refinement. The non-H atoms were refined with anisotropic thermal parameters and all of the H atoms were calculated in idealized positions and refined riding on their parent atoms. The asymmetric unit consists of four chemically equivalent but crystallographically independent complexes, four and three fourth DCM solvent molecules disordered over 10 positions, and two and a half pentane solvent molecules disordered over five positions. Due to the presence of four complexes in the asymmetric unit, a smaller unit cell was considered but this introduced ligand disorders that are not present in the larger unit cell. Additionally, a check for higher or missed symmetry did not present any new possibilities. Pseudo-symmetry was explored but also did not show any presence. Complex A shows no disorder while B has a disorder in the oxygen atoms of one nitro group. Complex C has one phosphorus atom and two of its phenyl rings disordered. A phenyl ring on the neighboring phosphorus is also disordered. Complex D shows disorder in only one phenyl ring but with both nitro groups' oxygen atoms disordered. One of the pentane molecules is disordered over seven carbon positions. In each disorder case, two parts were dependently refined. In the final cycle of refinement, 77525 reflections (of which 36301 are observed with I>2σ(I)) were used to refine 3958 parameters and the resulting R$_1$, wR$_2$ and S (goodness of fit) were 5.15%, 9.55% and 0.887, respectively. The refinement was carried out by minimizing the wR$_2$ function using F$^2$ rather than F values. R$_1$ is calculated to provide a reference to the conventional R value but its function is not minimized.

TABLE 9

Crystal data and structure refinement for cis-6-Ph

| | |
|---|---|
| Identification code | apow11 |
| Empirical formula | C370.75 H311.50 Au8 Cl9.50 N32 O16 P16 Pt4 |
| Formula weight | 8659.41 |
| Temperature | 100(2) K |
| Wavelength | 0.71073 Å |
| Crystal system | Triclinic |
| Space group | P$\bar{1}$ |
| Unit cell dimensions | a = 27.823(3) Å   α = 60.6370(10)°. |
| | b = 28.101(3) Å   β = 61.9650(10)°. |
| | c = 28.510(3) Å   γ = 84.409(2)°. |
| Volume | 16889(3) Å$^3$ |
| Z | 2 |
| Density (calculated) | 1.703 Mg/m$^3$ |
| Absorption coefficient | 5.327 mm$^{-1}$ |
| F(000) | 8467 |
| Crystal size | 0.08 × 0.06 × 0.02 mm$^3$ |
| Theta range for data collection | 0.84 to 27.50°. |
| Index ranges | −36 ≤ h ≤ 36, −36 ≤ k ≤ 36, −37 ≤ l ≤ 37 |
| Reflections collected | 236008 |
| Independent reflections | 77525 [R(int) = 0.1147] |
| Completeness to theta = 27.50° | 99.9% |
| Absorption correction | Integration |
| Max. and min. transmission | 0.8828 and 0.6814 |
| Refinement method | Full-matrix least-squares on F$^2$ |
| Data/restraints/parameters | 77525/54/3958 |
| Goodness-of-fit on F$^2$ | 0.877 |
| Final R indices [I > 2sigma(I)] | R1 = 0.0515, wR2 = 0.0955 [36301] |
| R indices (all data) | R1 = 0.1459, wR2 = 0.1142 |
| Largest diff. peak and hole | 3.284 and −2.923 e.Å$^{-3}$ |

R1 = Σ(||F$_o$| − |F$_c$||)/Σ|F$_o$|
wR2 = [Σ[w(F$_o^2$ − F$_c^2$)$^2$]/Σ[w(F$_o^2$)$^2$]]$^{1/2}$
S = [Σ[w(F$_o^2$ − F$_c^2$)$^2$]/(n-p)]$^{1/2}$
w = 1/[σ$^2$(F$_o^2$) + (m*p)$^2$ + n*p], p = [max(F$_o^2$,0) + 2* F$_c^2$]/3, m & n are constants.

Synthesis and Characterization of cis-6-Et.

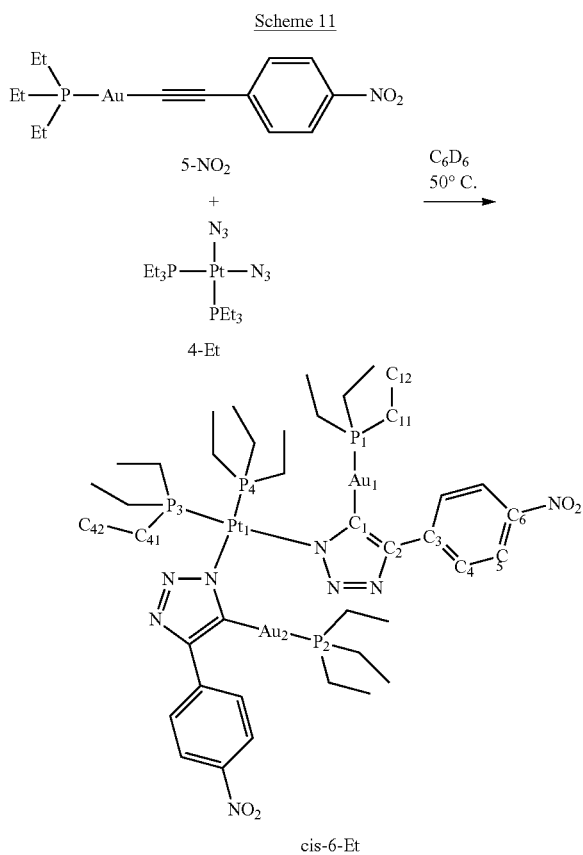

Scheme 11 cis-6-Et

Figure 8:
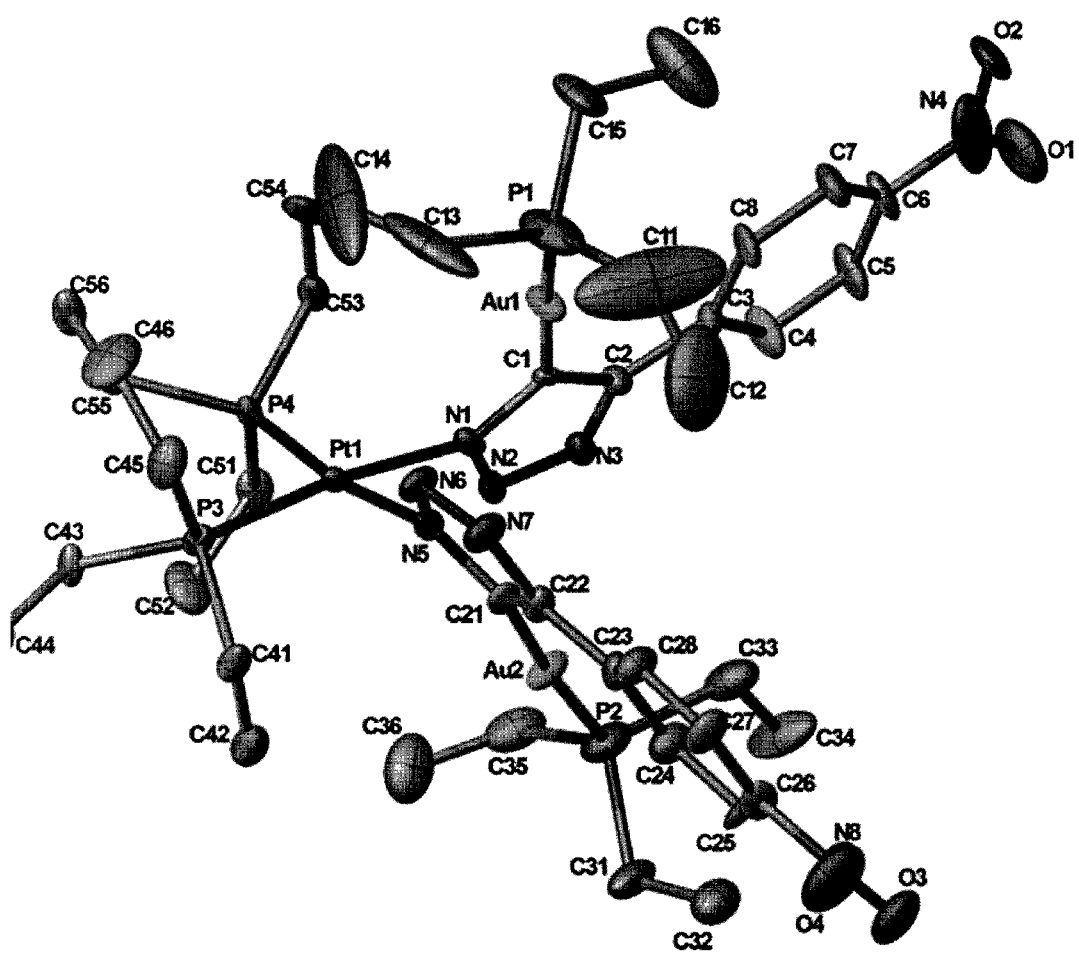
FIG. 8 shows the molecular structure of complex of cis-6-Et, according to an embodiment of the invention, as determined by single crystal X-ray diffraction experiments.

To a vial containing cis-(PEt$_3$)$_2$Pt(N$_3$)$_2$ (4-Et) (14.5 mg, 0.0282 mmol) and PEt$_3$Au$^J$C≡CC$_6$H$_4$NO$_2$ (5-NO$_2$) (26.0 mg, 0.0564 mmol), was added 0.6 ml C$_6$D$_6$. The suspension of the sparingly soluble platinum complex and soluble gold complex in benzene, was transferred to a sealable J. Young NMR tube, with an additional 0.2 ml of C$_6$D$_6$. The NMR tube was sealed and the mixture degassed using a freeze-pump-thaw cycle. The NMR tube was heated at 50° C. for 16 hours. Within the first 10 minutes all material dissolved, and the solution turned yellow/green in color. After 16 hours, the sample slowly cooled to room temperature and additional product crystallized overnight. The solid material, a 60:23:17 mixture of cis-6-Et, 8, and 7, was isolated by decanting the mother liquor, and washing with pentane. Pentane addition into a chloroform solution of the mixture selectively precipitates a mixture of cis-6-Et and 7 in crystalline form. Cis-6-Et was isolated from 7 by washing with cold benzene. Yield of cis-6-Et 14.2 mg, 35% yield. NMR $^1$H (300 MHz, CDCl$_3$): δ 8.31 (d, $^3J_{HH}$=8.95 Hz, 4H, H4), 7.83 (d, $^3J_{HH}$=8.95 Hz, 4H, 5H), 1.77 (d, $^3J_{HH}$=8.95 Hz, 6H, H11D), 1.77 (d, $^3J_{HH}$=8.95 Hz, 6H, H11A), 1.73 (ddq, $^2J_{HH}$=13.2 Hz, $^2J_{PH}$=13.2 Hz, $^3J_{HH}$=7.7 Hz, 6H, H$_{41}$B), 1.29 (ddq, $^2J_{HH}$=13.6 Hz, $^2J_{PH}$=13.6 Hz, $^3J_{HH}$=7.6 Hz, 61-1, H41A), 1.02 (dt, $^3J_{PH}$=8.0 Hz, $^3J_{HH}$=7.9 Hz, 18H, H42), 0.99 (dt, $^3J_{PH}$=9.1 Hz, $^3J_{HH}$=8.4 Hz, 18H, H12). $^{13}$C NMR Shifts (indirect detection through $^1$H-$^{13}$C gHMBC and $^1$H-$^{13}$C gHSQC (500 MHz, CDCl$_3$)): δ 150.7 (C2), 144.3 (C6), 144.1 (C3), 124.8 (C4), 123.5 (C5), 17.4 (C11), 14.9 (C41), 8.9 (C12), 8.5 (C42). NMR $^{31}$P (121.4 MHz, CDCl$_3$): δ 40.08 (s, (P1)), 1.53 (s, w/satellites: $^1J_{Pt-P}$=2974 Hz, (P3)). Anal. Calcd for C$_{40}$H$_{68}$Au$_2$N$_8$O$_4$P$_4$Pt: C, 33.41; H, 4.77; N, 7.79. Found: C, 33.49; H, 4.61; N, 7.90. The molecular structure for cis-6-Et from x-ray data is shown in FIG. 8.

X-Ray experimental for cis-6-Et: X-Ray Intensity data were collected at 100 K on a Bruker DUO diffractometer using MoKα radiation (λ=0.71073 Å) and an APEXII CCD area detector.

Raw data frames were read by program SAINT[1] and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces.

The structure was solved and refined in SHELXTL6.1, using full-matrix least-squares refinement. The non-H atoms were refined with anisotropic thermal parameters and all of the H atoms were calculated in idealized positions and refined riding on their parent atoms. The asymmetric unit consists of two platinum complexes and five benzene solvent molecules. The benzene molecules were disordered and could not be modeled properly, thus program SQUEEZE, a part of the PLATON package of crystallographic software, was used to calculate the solvent disorder area and remove its contribution to the overall intensity data. The C42, C34 and C36 units were disordered and refined in two parts with their site occupation factors fixed (after refinements) at a ratio of 60/40. The N8' nitro group did not refine properly thus it was constrained to maintain a geometry similar to the N4' nitro group. In the final cycle of refinement, 136267 reflections (of which 19923 are observed with I>2σ(I)) were used to refine 1048 parameters and the resulting R$_1$, wR$_2$ and S (goodness of fit) were 6.27%, 16.55% and 1.066, respectively. The refinement was carried out by minimizing the wR$_2$ function using F$^2$ rather than F values. R$_1$ is calculated to provide a reference to the conventional R value but its function is not minimized. The highest residual peaks are high although they do lie close to the gold centers. Models of the structure were refined with and without absorption corrections and the peaks persisted.

TABLE 10

Crystal data and structure refinement for cis-6-Et.

| | |
|---|---|
| Identification code | tre05 |
| Empirical formula | C55 H83 Au2 N8 O4 P4 Pt |
| Formula weight | 1633.20 |
| Temperature | 100(2) K |
| Wavelength | 0.71073 Å |
| Crystal system | Triclinic |
| Space group | P$\bar{1}$ |
| Unit cell dimensions | a = 14.963(2) Å    α = 70.137(3)°. |
| | b = 19.646(3) Å    β = 86.619(3)°. |
| | c = 23.512(3) Å    γ = 76.690(3)°. |
| Volume | 6324.7(15) Å$^3$ |
| Z | 4 |
| Density (calculated) | 1.715 Mg/m$^3$ |
| Absorption coefficient | 6.993 mm$^{-1}$ |
| F(000) | 3188 |
| Crystal size | 0.17 × 0.13 × 0.03 mm$^3$ |
| Theta range for data collection | 1.13 to 27.50°. |
| Index ranges | −19 ≤ h ≤ 19, −25 ≤ k ≤ 25, −30 ≤ l ≤ 30 |
| Reflections collected | 136267 |
| Independent reflections | 29055 [R(int) = 0.0678] |
| Completeness to theta = 27.50° | 100.0% |
| Absorption correction | Integration |
| Max. and min transmission | 0.8023 and 0.3920 |
| Refinement method | Full-matrix least-squares on F$^2$ |
| Data/restraints/parameters | 29055/3/1048 |
| Goodness-of-fit on F$^2$ | 1.066 |
| Final R indices [I > 2sigma(I)] | R1 = 0.0627, wR2 = 0.1655 [19923] |

TABLE 10-continued

Crystal data and structure refinement for cis-6-Et.

| | |
|---|---|
| R indices (all data) | R1 = 0.0882, wR2 = 0.1737 |
| Largest diff. peak and hole | 12.846 and −6.455 e.Å$^{-3}$ |

$R1 = \Sigma(||F_o| - |F_c||)/\Sigma|F_o|$ $wR2 = [\Sigma[w(F_o^2 - F_c^2)^2]/\Sigma[w(F_o^2)^2]]^{1/2}$ $S = [\Sigma[w(F_o^2 - F_c^2)^2]/(n-p)]^{1/2}$ $w = 1/[\sigma^2(F_o^2) + (m*p)^2 + n*p]$, $p = [\max(F_o^2, 0) + 2* F_c^2]/3$, m & n are constants.

Synthesis and Characterization of 8.

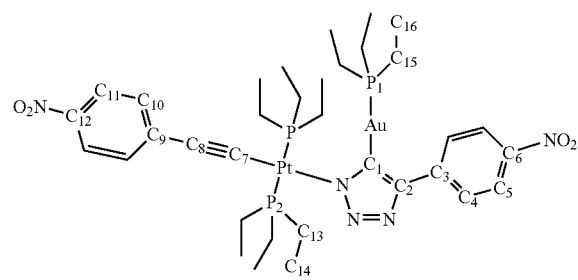

To a vial containing cis-(PEt$_3$)$_2$Pt(N$_3$)$_2$ (4-Et) (14.5 mg, 0.0282 mmol) and PEt$_3$Au$^I$C≡CC$_6$H$_4$NO$_2$ (5-Et) (26.0 mg, 0.0564 mmol), was added 0.6 ml C$_6$D$_6$. The only sparingly soluble platinum complex suspension and soluble gold complex in benzene was transferred to a sealable J. Young NMR tube, with an additional 0.2 ml of C$_6$D$_6$. The NMR tube was sealed and the mixture degassed with a freeze-pump-thaw cycle. The NMR tube was heated at 50° C. for 16 hours. Within the first 10 minutes all material dissolved and the solution turned yellow/green in color. After 16 hours, the sample was immediately filtered to remove a mixture of crystalline solid which consisted predominately of cis-6-Et and 7, with a very minor amount of 8. The volume of the benzene filtrate was reduced via slow evaporation by approximately 0.1 ml, and filtering was repeated. This filtrate was reduced to approximately 0.2 ml by slow evaporation to yield additional crystalline material. This additional crystalline material was a 95:5 mixture of 8, and 7 by NMR that was isolated by decanting the mother liquor, and washing the solid material with pentane. Pure 8 was not obtained via further fractional recrystallizations from the 5 molar percent impurity of 7. The yield of 8 was 19.8% yield based on platinum. NMR $^1$H (300 MHz, CDCl$_3$): δ 8.59 (d, $^3J_{HH}$=8.2 Hz, 2H, (H4)), 8.17 (d, $^3J_{HH}$=8.2 Hz, 2H, (H5)), 8.12 (d, $^3J_{HH}$=8.2 Hz, 2H, (H11)), 7.31 (d, $^3J_{HH}$=8.2 Hz, 2H, (H10)), 1.92 (dq, $^2J_{PH}$=8.5 Hz, $^3J_{HH}$=7.9 Hz, (H15)), 1.82 (d, $^3J_{HH}$=8.2 Hz, (H13A)), 1.77 (ddq, $^2J_{HH}$=8.1 Hz, $^2J_{PH}$=8.1 Hz, $^3J_{HH}$=7.3 Hz, (H$_{13}$B)), 1.34 (dt, $^3J_{PH}$=17.6 Hz, $^3J_{HH}$=7.7 Hz, (H16)), 1.18 (dt, $^3J_{PH}$=16.1 Hz, $^3J_{HH}$=8.1 Hz, (H14)). $^{13}$C NMR Shifts (indirect detection through $^1$H-$^{13}$C gHMBC and $^1$H-$^{13}$C gHSQC (500 MHz, CDCl$_3$)): δ 151.8 (C2), 144.9 (C6), 144.6 (C12), 143.6 (C3), 135.8 (C9), 131.1 (C10), 125.1 (C4), 123.8 (C5), 123.7 (C11), 106.8 (C8), 17.9 (C15), 14.4 (C13), 8.9 (C16), 8.1 (C14), (note: C1 and C7 are not observed). NMR $^{31}$P (121.4 MHz, CDCl$_3$): δ 40.0 (s, (P1)), 13.8 (s, w/satellites: $^1J_{Pt-P}$=2458.1 Hz, (P2)).

Synthesis and Characterization of 7.

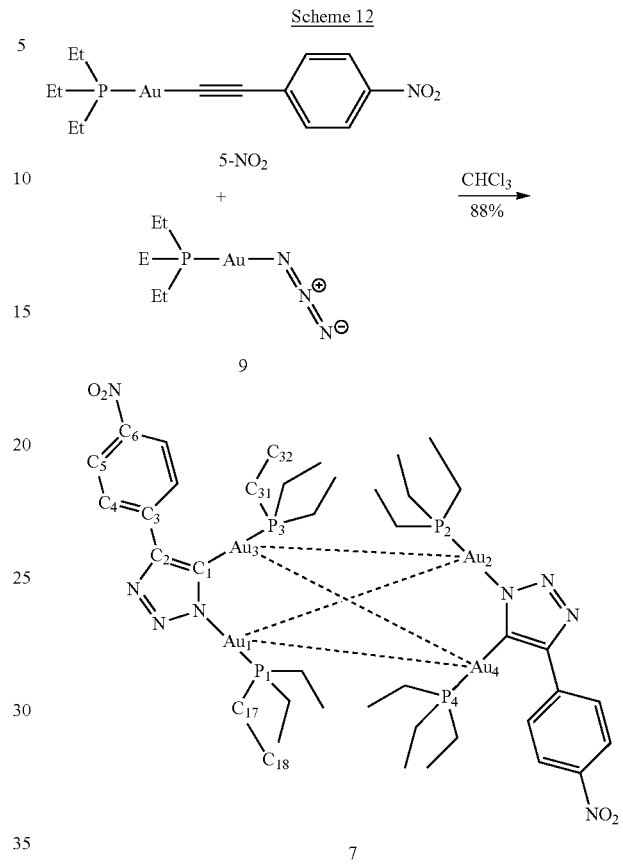

Figure 9:
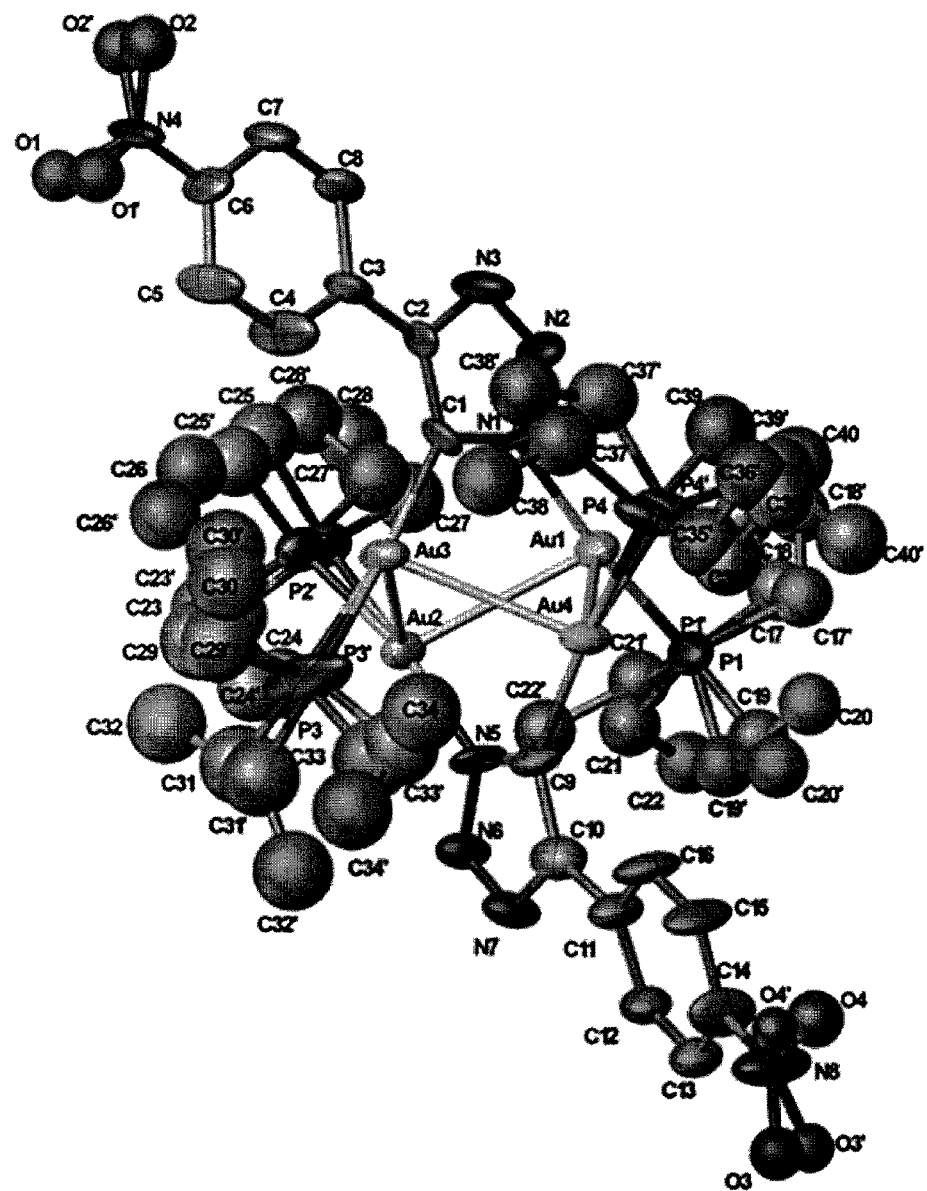
FIG. 9 shows the molecular structure of complex of 7, according to an embodiment of the invention, as determined by single crystal X-ray diffraction experiments.

To a 2 ml chloroform solution of PEt$_3$Au$^I$C≡CC$_6$H$_4$NO$_2$ (5-NO$_2$) (60 mg, 0.130 mmol) was added PEt$_3$Au$^I$N$_3$ (9) (46.5 mg, 0.130 mmol). This reaction mixture was stirred overnight, yielding a dark gold/orange solution containing 7, which was isolated by removing the solvent in-vacuo, and washing the residue with pentane. Analytically pure material could be obtained by diffusion of pentane into a CH$_2$Cl$_2$ solution of 7, which yields long, needle-like yellow crystals in 88% yield (93 mg, 0.0568 mmol). NMR $^1$H (300 MHz, CDCl$_3$): δ 8.70 (d, $^3J_{HH}$=8.9 Hz, 4H, H5), 8.14 (d, $^3J_{HH}$=8.69 Hz, 4H, H4), 1.51 (dq, $^2J_{PH}$=7.6 Hz, $^3J_{HH}$=7.6 Hz, 12H, H17), 1.47 (dq, $^2J_{PH}$=7.5 Hz, $^3J_{HH}$=7.5 Hz, 12H, H31), 1.10 (dt, $^3J_{PH}$=6.65 Hz, $^3J_{HH}$=7.71 Hz, 18H, H32), 1.04 (dt, $^3J_{PH}$=6.65 Hz, $^3J_{HH}$=7.71 Hz, 18H, H18). $^{13}$C NMR Shifts (indirect detection through $^1$H-$^{13}$C gHMBC and $^1$H-$^{13}$C gHSQC (500 MHz, CDCl$_3$)): δ 151.1 (C2), 145.1 (C6), 143.7 (C3), 126.0 (C4), 123.6 (C5), 17.2 (C31), 16.6 (C17), 8.5 (C32), 8.5 (C18). NMR $^{31}$P{$^1$H} (121.4 MHz, CDCl$_3$): δ 31.7 (s, P3/P4), 20.8 (s, P1/P2). Anal. Calcd for C$_{40}$H$_{68}$Au$_4$N$_8$O$_4$P$_4$: C, 29.35; H, 4.19; N, 6.85. Found: C, 29.42; H, 4.29; N, 6.98. The molecular structure for 7 from x-ray data is shown in FIG. 9.

X-Ray experimental for 7: X-Ray Intensity data were collected at 100 K on a Bruker DUO diffractometer using MoKα radiation (λ=0.71073 Å) and an APEXII CCD area detector.

Raw data frames were read by program SAINT[1] and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces.

The structure was solved and refined in SHELXTL6.1, using full-matrix least-squares refinement. The non-H atoms were refined with anisotropic thermal parameters and all of the H atoms were calculated in idealized positions and refined riding on their parent atoms. The asymmetric unit consists of one $Au_4$ cluster and one diethyl ether solvent molecule disordered over three positions. The solvent molecules were disordered and could not be modeled properly, thus program SQUEEZE, a part of the PLATON package of crystallographic software, was used to calculate the solvent disorder area and remove its contribution to the overall intensity data. All four triethylphosphine ligands are wholly disordered and each was refined in two parts. Restrictions were applied using SADI to maintain equal P—C and C—C bonds in those ligands as well as using EADP to maintain equivalent displacement parameters among similar atoms. Both nitro groups have their oxygen atoms disordered and each was refined in two parts. It is worth noting here that all possible merohedral twinning possibilities were explored but none fit. In the final cycle of refinement, 9435 reflections (of which 6179 are observed with $I>2\sigma(I)$) were used to refine 483 parameters and the resulting $R_1$, $wR_2$ and S (goodness of fit) were 7.53%, 16.93% and 1.048, respectively. The refinement was carried out by minimizing the $wR_2$ function using $F^2$ rather than F values. $R_1$ is calculated to provide a reference to the conventional R value but its function is not minimized.

TABLE 11

Crystal data and structure refinement for 7.

| | |
|---|---|
| Identification code | apow9 |
| Empirical formula | C44 H78 Au4 N8 O5 P4 |
| Formula weight | 1710.89 |
| Temperature | 100(2) K |
| Wavelength | 0.71073 Å |
| Crystal system | Rhombohedral |
| Space group | R-3 |
| Unit cell dimensions | a = 46.159(2) Å, α = 90°. |
| | b = 46.159(2) Å, β = 90°. |
| | c = 13.0682(6) Å, γ = 120°. |
| Volume | 24113.7(18) Å$^3$ |
| Z | 18 |
| Density (calculated) | 2.121 Mg/m$^3$ |
| Absorption coefficient | 11.086 mm$^{-1}$ |
| F(000) | 14652 |
| Crystal size | 0.15 × 0.08 × 0.04 mm$^3$ |
| Theta range for data collection | 1.53 to 25.00°. |
| Index ranges | $-51 \leq h \leq 51$, $-50 \leq k \leq 54$, $-15 \leq l \leq 15$ |
| Reflections collected | 78284 |
| Independent reflections | 9435 [R(int) = 0.1022] |
| Completeness to theta = 25.00° | 100.0% |
| Absorption correction | Integration |
| Max. and min. transmission | 0.6976 and 0.2818 |
| Refinement method | Full-matrix least-squares on F$^2$ |
| Data/restraints/parameters | 9435/255/483 |
| Goodness-of-fit on F$^2$ | 1.048 |
| Final R indices [I > 2sigma(I)] | R1 = 0.0753, wR2 = 0.1693 [6179] |
| R indices (all data) | R1 = 0.1169, wR2 = 0.1832 |
| Largest diff. peak and hole | 2.746 and −1.392 e.Å$^{-3}$ |

$R1 = \Sigma(||F_o| - |F_c||)/\Sigma|F_o|$
$wR2 = [\Sigma[w(F_o^2 - F_c^2)^2/\Sigma[w(F_o^2)^2]]^{1/2}$
$S = [\Sigma[w(F_o^2 - F_c^2)^2]/(n-p)]^{1/2}$
$w = 1/[\sigma^2(F_o^2) + (m*p)^2 + n*p]$, $p = [\max(F_o^2, 0) + 2*F_c^2]/3$, m & n are constants.

Synthesis and Characterization of $[Au^I(C{\equiv}C\text{-}4\text{-}C_6H_4NO_2)]_2$ (μ-dppm) (10).

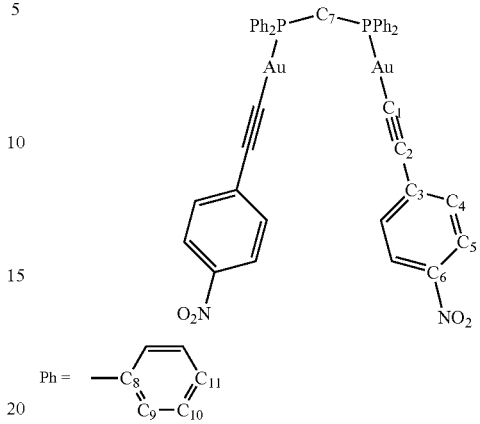

In a 100 ml Schlenk flask, 80 mg sodium metal (3.48 mmol) was added to 20 mL of dry methanol under argon. After hydrogen gas evolution ceased, the sodium-methoxide in methanol solution was transferred via a syringe under argon into a second Schlenk flask containing 200 mg $Au_2$(μ-dppm)$_2$Cl$_2$ (0.16 mmol) and 51 mg 2-ethynyl-4-nitrobenzene (0.34 mmol). The pale yellow reaction mixture was stirred under argon overnight. The product was isolated as a pale-yellow powder by filtration and washed with 5 mL of dry methanol and 10 mL of diethyl ether. After removing all volatiles in vacuo, complex 10 was obtained in 92% yield (158 mg). $^1$H NMR (500 MHz, CDCl$_3$) δ 7.98(d, $^3J_{HH}$=8.3 Hz, 4H, H5), 7.64 (dt, $^3J_{PH}$=8.2 Hz, $^3J_{HH}$=7.1 Hz, 8H, H9), 7.52 (d, $^3J_{HH}$=8.3 Hz, 4H, H4), 7.46 (dd, $^3J_{HH}$=7.1 Hz, 4H, H11), 7.37 (dd, $^3J_{HH}$=7.1 Hz, 8H, H10), 3.62 (dd, $^3J_{PH}$=10.3 Hz, 2H, H7). $^{13}$C{1H} NMR (126 MHz, CDCl$_3$) δ 145.7 (C6), 141.4 (C1), 133.4 (C9), 132.7 (C4), 132.2 (C3, C11), 129.4 (C10), 129.0 (C8), 123.1 (C5) 103.5 (C2), 29.5 (C7). $^{31}$P NMR (121.1 MHz, CDCl$_3$) δ 31.73 (s). Anal. Calcd. For $C_{41}H_{30}Au_2N_2O_4P_2$: C, 46.00; H, 2.82; N, 2.62. Found: C, 46.05; H, 2.69; N, 2.63.

Synthesis and Characterization of 11.

Scheme 13

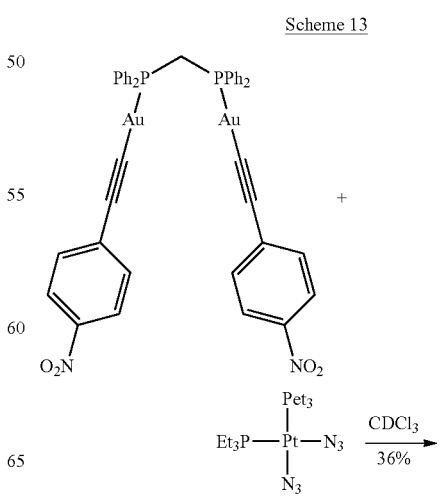

-continued

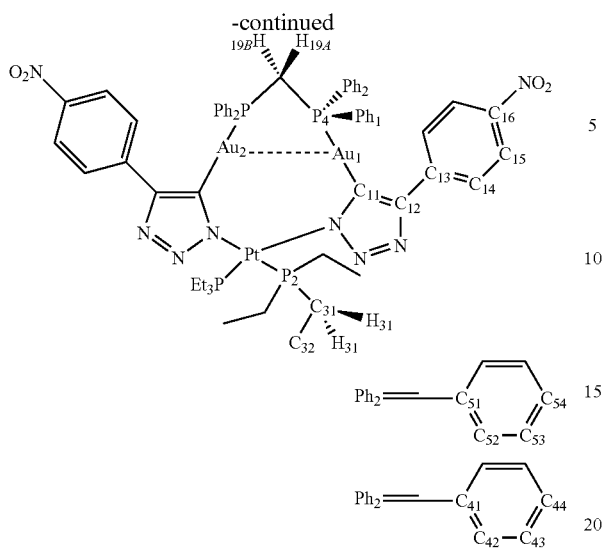

Figure 10:
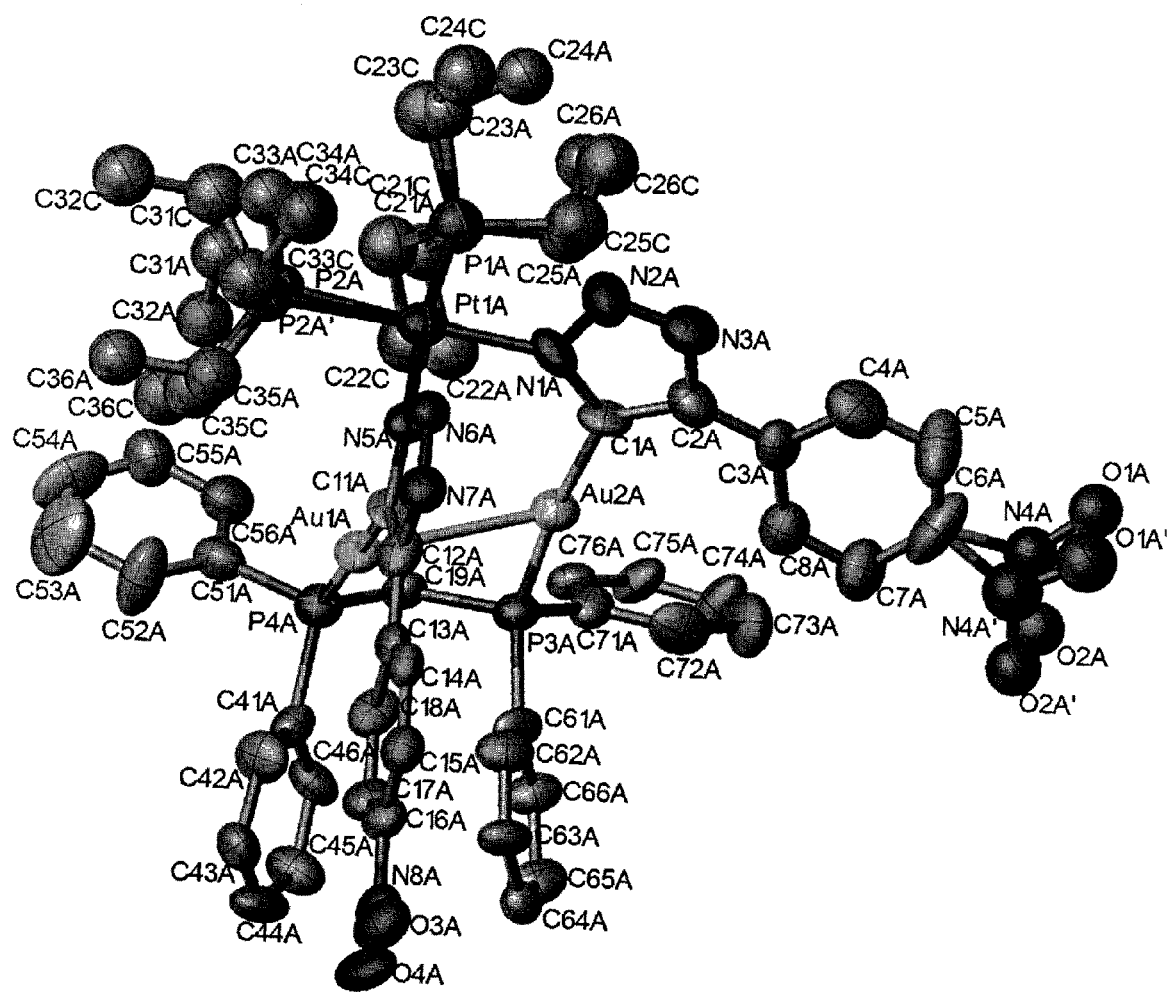
FIG. 10 shows the molecular structure of complex of cis-11, according to an embodiment of the invention, as determined by single crystal X-ray diffraction experiments.

A sealable NMR tube was charged with 20 mg of 4-Et (0.039 mmol), 45 mg of 10 (0.042 mmol) and 1.5 mL CDCl$_3$. Yellow crystals formed upon standing at room temperature for 2 days. Crystals were isolated by decanting the supernatant and washing with 1 mL of chloroform and 5 mL of diethyl ether. The crystalline material was dried in vacuo to provide 11 in 36% yield (22 mg). $^1$H NMR (500 MHz, DMSO-d6) δ 8.39 (d, $^3J_{HH}$=9 Hz, 4H, H14), 7.95 (d, $^3J_{HH}$=9 Hz, 4H, H15), 7.88 (m, 4H, H42), 7.66 (dt, $^3J_{PH}$=6.9 Hz, $^3J_{HH}$=6.9 Hz, 4H, H52), 7.51 (m, 6H, 43-H, H44), 7.37 (dd, $^3J_{HH}$=7.5 Hz, 2H, H54), 7.18 (dd, $^3J_{HH}$=7.6 Hz, 4H, H53), 5.20 (dt, $^3J_{PH}$=$^3J_{HH}$=13.4 Hz, 1H, H$_{19}$B), 3.70 (dt, $^3J_{PH}$=14.5 Hz, $^3J_{HH}$=10.9 Hz, 1H, H19A), 1.62 (ddq, $^2J_{PH}$=15.3 Hz, $^3J_{HH}$=$^2J_{HH}$=7.7 Hz, 6H, H31), 1.51 (ddq, $^2J_{PH}$=15.4 Hz, $^3J_{HH}$=$^2J_{HH}$=7.6 Hz, 6H, H31), 0.98 (dt, $^3J_{PH}$=16.3 Hz, $^3J_{HH}$=7.5 Hz, 18H, H32). $^{13}$C{$^1$H} NMR (126 MHz, DMSO-d) δ 170.5 (C11), 149.6 (C12), 144.5 (C16), 144.3 (C13), 134.4 (C52), 132.8 (C42), 132.2 (C54), 131.8 (C44, C41), 130.4 (C51), 129.6 (C43), 129.3 (C53), 125.3 (C14), 124.1 (C15), 23.3 (C19), 14.1 (C31), 8.3 (C32). $^{31}$P{$^1$H} NMR (121.1 MHz, DMSO-d6) δ 36.4 (s, P4), −1.6 (s, P2). Anal. Calcd. For C$_{53}$H$_{60}$Au$_2$O$_4$N$_8$P$_4$Pt: C, 40.14; H, 3.87; N, 7.07. Found: C, 40.08; H, 3.74; N, 6.96. The molecular structure for 11 from x-ray data is shown in FIG. 10.

X-Ray experimental for 11: X-Ray Intensity data were collected at 100 K on a Bruker DUO diffractometer using MoKα radiation (λ=0.71073 Å) and an APEXII CCD area detector. Raw data frames were read by program SAINT$^1$ and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces. The structure was solved and refined in SHELXTL6.1, using full-matrix least-squares refinement. The non-H atoms were refined with anisotropic thermal parameters and all of the H atoms were calculated in idealized positions and refined riding on their parent atoms. In complex A, N4A nitro groups are disordered and were refined in two parts. Both P1A and P2A are disordered and were refined in two parts with their respective ethyl groups. In molecule B, only the N1B nitro groups are disordered. Partially disordered chloroform molecules as well as disordered pentane molecules are also present in the structure. In all, the asymmetric unit consists of two PtAu$_2$ complexes, and three and a third chloroform molecules disordered over seven general and two symmetry positions. Attempts to remove the solvent area contributions to the overall intensity of the data failed because of the disordered partial solvent molecule's proximity to the complexes, thus good void calculations were not possible. In the final cycle of refinement, 23814 reflections (of which 13830 are observed with I>2σ(I)) were used to refine 1328 parameters and the resulting R$_1$, wR$_2$ and S (goodness of fit) were 6.89%, 18.71% and 1.365, respectively. The refinement was carried out by minimizing the wR$_2$ function using F$^2$ rather than F values. R$_1$ is calculated to provide a reference to the conventional R value but its function is not minimized.

TABLE 12

Crystal data and structure refinement for 11.

| | |
|---|---|
| Identification code | xy04 |
| Empirical formula | C111.33 H114.80 Au4 Cl0.56 N16 O8 P8 Pt2 |
| Formula weight | 3250.49 |
| Temperature | 100(2) K |
| Wavelength | 0.71073 Å |
| Crystal system | Rhombohedral |
| Space group | R-3 |
| Unit cell dimensions | a = 42.079(3) Å    α = 90°. |
| | b = 42.079(3) Å    β = 90°. |
| | c = 39.683(3) Å    γ = 120°. |
| Volume | 60851(8) Å$^3$ |
| Z | 18 |
| Density (calculated) | 1.597 Mg/m$^3$ |
| Absorption coefficient | 6.543 mm$^{-1}$ |
| F(000) | 28084 |
| Crystal size | 0.14 × 0.13 × 0.09 mm$^3$ |
| Theta range for data collection | 1.52 to 25.00°. |
| Index ranges | −49 ≤ h ≤ 24, 0 ≤ k ≤ 50, 0 ≤ l ≤ 47 |
| Reflections collected | 23814 |
| Independent reflections | 23814 [R(int) = 0.0000] |
| Completeness to theta = 25.00° | 100.0% |
| Absorption correction | Semi-empirical from equivalents |
| Max. and min. transmission | 0.5844 and 0.4589 |
| Refinement method | Full-matrix least-squares on F$^2$ |
| Data/restraints/parameters | 23814/108/1328 |
| Goodness-of-fit on F$^2$ | 1.365 |
| Final R indices [I > 2sigma(I)] | R1 = 0.0689, wR2 = 0.1871 [13830] |
| R indices (all data) | R1 = 0.1422, wR2 = 0.2306 |
| Largest diff. peak and hole | 3.934 and −1.762 e.Å$^{-3}$ |

R1 = Σ(||F$_o$| − |F$_c$||)/Σ|F$_o$|
wR2 = [Σ[w(F$_o^2$ − F$_c^2$)$^2$]/Σ[w(F$_o^2$)$^2$]]$^{1/2}$
S = [Σ[w(F$_o^2$ − F$_c^2$)$^2$]/(n-p)]$^{1/2}$
w = 1/[σ$_2$(F$_o^2$) + (m*p)$^2$ + n*p], p = [max(F$_o^2$,0) + 2* F$_c^2$]/3, m & n are constants.

Synthesis of Homo-tetranuclear Complex 14.

Scheme 13

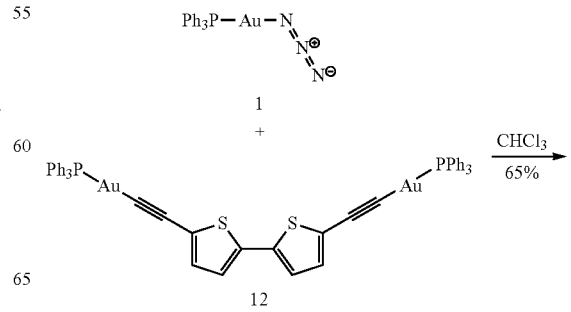

-continued

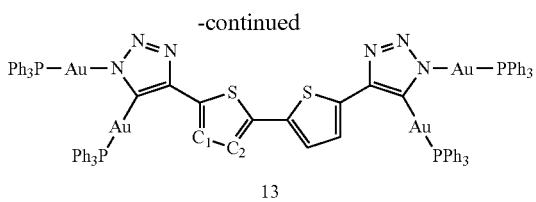

13

Synthesis of 13

To a 10 ml CHCl$_3$ solution of [PPh$_3$Au$^I$]$_2$[C≡C(C$_4$H$_2$S)$_2$C≡C] (44 mg, 0.039 mmol) is added PPh$_3$Au$^I$N$_3$ (40 mg, 0.080 mmol). This reaction solution is stirred for 1 h, at which point the solvent is removed in-vacuo. The residue is then extracted with 5 ml dichloromethane and filtered, and the volume of the filtrate is reduced to ~1 ml. Addition of 5 ml pentane precipitates the product as a brown-yellow solid in 65% (54 mg) yield. $^1$H NMR (300 MHz, CDCl$_3$) δ 7.46-7.53 (m, PPh$_3$-H), δ 7.02 (d, $^3J_{HH}$=3.78 Hz, 2H, H2) δ 6.62 (d, $^3J_{HH}$=3.78 Hz, 2I-I, H1). $^{31}$P NMR (121.1 MHz, CDCl$_3$) δ 44.52 (s, C—Au—P), δ 32.26 (bs, N—Au—P).

One of the indications of formation of IClick product is from phosphine NMR spectra. The phosphine signal of gold thiopheneacetylide compound is at δ 41.59 ppm and the gold azide phosphine signal is at δ 31.37 ppm. After the reaction, the corresponding starting material phosphine signals disappeared and two new signals arise at δ 44.52 ppm and δ 32.26 ppm. The other is from proton NMR. The H1 doublet chemical signal of gold thiopheneacetylide compound is at 6.92 ppm while in the isolated product, this doublet signal shifted to 6.62 ppm. And the IR spectra gives direct evidence that cycloaddition reaction happened based on the azide stretch at 2149 cm$^{-1}$ disappeared for the final product.

It should be understood that the examples and embodiments described herein are for illustrative purposes only and that various modifications or changes in light thereof will be suggested to persons skilled in the art and are to be included within the spirit and purview of this application.

We claim:

1. A bimetallic substituted triazole complex, comprising one or more 1,2,3-triazole units where at least one of the triazole units is substituted by two metal ions at the 1 and 4 or 5 positions.

2. The complex of claim 1, wherein the one or more triazole units substituted with two metal ions are further substituted independently with an organic substituent at the 4 or 5 positions wherein the organic substituent is selected from C$_1$-C$_{30}$ alkyl, C$_6$-C$_{22}$ aryl, C$_7$-C$_{30}$ alkylaryl, C$_7$-C$_{30}$ arylalkyl, C$_2$-C$_{29}$ heteroaryl, C$_3$-C$_{30}$ alkylheteroaryl, C$_3$-C$_{30}$ heteroarylalkyl, C$_2$-C$_{30}$ alkenyl, C$_8$-C$_{30}$ alkenylaryl, C$_8$-C$_{30}$ arylalkenyl, C$_4$-C$_{30}$ alkenylheteroaryl, and C$_4$-C$_{30}$ heteroarylalkenyl.

3. The complex of claim 1, wherein the metal ions are independently group 3-16 metal.

4. The complex of claim 1, wherein the metal ions are independently Au, Ni, Pd, Pt, Ru, Fe, Mn, Rh, Ir, Cr, Cu, or W.

5. The complex of claim 1, wherein one or both of the metal ions of the bimetallic substituted triazole unit form a cluster complex.

6. The complex of claim 1, further comprising at least one ligand to at least one metal ion.

7. The complex of claim 6, wherein the ligand is independently any phosphorous-based ligand, nitrogen-based ligand, cyclopentadienyl-based ligand, carbon monoxide, nitrosyl, alkyl, aryl, or pincer-type ligand.

8. The complex of claim 1, comprising a plurality of triazole units wherein at least one metal is attached to two triazole units.

9. The complex of claim 8, wherein a multiplicity of triazole units are connected by a multiplicity of metal ions as a linear polymeric chain or a polymeric network.

10. The complex of claim 8, wherein the polymeric network comprises tetrahedral metal ions.

11. The complex of claim 10, wherein the polymeric network comprises octahedral metal ions.

12. The complex of claim 11, wherein the polymeric network is a two-dimensional network.

13. The complex of claim 11, wherein the polymeric network is a three-dimensional network.

14. A method for the preparation of the bimetallic substituted triazole complex of claim 1, comprising:
providing at least one metal acetylide;
providing at least one metal azide; and
combining the metal acetylide and the metal azide; wherein the azide and acetylide undergo cycloaddition to form a triazole ring, wherein the metal of the metal azide is a substituent at the 1 position of the triazole ring and the metal of the metal acetylide is a substituent at the 4 or 5 position of the triazole ring.

15. The method of claim 14, wherein the metal azide is a metal and 1 to 6 azide groups.

16. The method of claim 14, wherein the metal acetylide is a metal and 1 to 6 acetylide groups.

17. The method of claim 14, wherein the acetylide groups are independently unsubstituted or substituted with an organic group selected from C$_1$-C$_{30}$ alkyl, C$_6$-C$_{22}$ aryl, C$_7$-C$_{30}$ alkylaryl, C$_7$-C$_{30}$ arylalkyl, C$_2$-C$_{29}$ heteroaryl, C$_3$-C$_{30}$ alkylheteroaryl, C$_3$-C$_{30}$ heteroarylalkyl, C$_2$C$_{30}$ alkenyl, C$_8$-C$_{30}$ alkenylaryl, C$_8$-C$_{30}$ arylalkenyl, C$_4$-C$_{30}$ alkenylheteroaryl, and C$_4$-C$_{30}$ heteroarylalkenyl.

18. The method of claim 14, wherein the cycloaddition reaction is catalyzed by a copper (I) salt.

* * * * *

UNITED STATES PATENT AND TRADEMARK OFFICE
CERTIFICATE OF CORRECTION

PATENT NO.         : 8,889,879 B2
APPLICATION NO.    : 13/872544
DATED              : November 18, 2014
INVENTOR(S)        : Adam Steven Veige et al.

Page 1 of 1

It is certified that error appears in the above-identified patent and that said Letters Patent is hereby corrected as shown below:

In the specification

Column 25,
Lines 14-15, "$Au_2$" should read --$Au_2 - P_3$--.

Column 27,
Line 59, "$H_{41}B$)" should read --II41B)--.
Line 60, "61-1, H41A)" should read --6H, H41A)--.

Column 28,
Line 63, "Max. and min transmission" should read --Max. and min. transmission--.

Column 29,
Line 57, "($H_{13}B$))" should read --(H13B))--.

Column 33,
Line 19, "$Ph_2$" should read --$Ph_1$--.
Line 35, "($H_{19}B$)" should read --(H19B)--.

Column 35,
Line 20, "21-I, H1)" should read --2H, H1)--.

Signed and Sealed this
Sixth Day of October, 2015

Michelle K. Lee
*Director of the United States Patent and Trademark Office*

UNITED STATES PATENT AND TRADEMARK OFFICE
CERTIFICATE OF CORRECTION

PATENT NO.        : 8,889,879 B2
APPLICATION NO.   : 13/872544
DATED             : November 18, 2014
INVENTOR(S)       : Adam Steven Veige et al.

It is certified that error appears in the above-identified patent and that said Letters Patent is hereby corrected as shown below:

In the specification

Column 25,
Lines 14-15, "$Au_2$" should read --$Au_2 - P_3$--.

Column 27,
Line 59, "$H_{41}B)$" should read --H41B)--.
Line 60, "61-1, H41A)" should read --6H, H41A)--.

Column 28,
Line 63, "Max. and min transmission" should read --Max. and min. transmission--.

Column 29,
Line 57, "$(H_{13}B))$" should read --(H13B))--.

Column 33,
Line 19, "$Ph_2$" should read --$Ph_1$--.
Line 35, "$(H_{19}B)$" should read --(H19B)--.

Column 35,
Line 20, "21-I, H1)" should read --2H, H1)--.

This certificate supersedes the Certificate of Correction issued October 6, 2015.

Signed and Sealed this
Twenty-ninth Day of March, 2016

Michelle K. Lee
*Director of the United States Patent and Trademark Office*